(12) United States Patent
Ota et al.

(10) Patent No.: US 12,226,480 B2
(45) Date of Patent: Feb. 18, 2025

(54) COMBINATION DRUG INCLUDING TLR7 AGONIST

(71) Applicant: SUMITOMO PHARMA CO., LTD., Osaka (JP)

(72) Inventors: Yosuke Ota, Osaka (JP); Takeshi Otsubo, Toyonaka (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 627 days.

(21) Appl. No.: 16/772,846

(22) PCT Filed: Dec. 20, 2018

(86) PCT No.: PCT/JP2018/047011
§ 371 (c)(1),
(2) Date: Jun. 15, 2020

(87) PCT Pub. No.: WO2019/124500
PCT Pub. Date: Jun. 27, 2019

(65) Prior Publication Data
US 2021/0170022 A1    Jun. 10, 2021

(30) Foreign Application Priority Data
Dec. 21, 2017   (JP) ................ 2017-244675

(51) Int. Cl.
| | | |
|---|---|---|
| A61K 39/395 | (2006.01) | |
| A61K 31/437 | (2006.01) | |
| A61K 31/505 | (2006.01) | |
| A61K 31/522 | (2006.01) | |
| A61P 35/00 | (2006.01) | |

(52) U.S. Cl.
CPC ........ *A61K 39/3955* (2013.01); *A61K 31/437* (2013.01); *A61K 31/505* (2013.01); *A61K 31/522* (2013.01); *A61P 35/00* (2018.01)

(58) Field of Classification Search
CPC ................ A61K 2300/00; A61K 45/06; A61K 2039/505
See application file for complete search history.

(56) References Cited

U.S. PATENT DOCUMENTS

| | | |
|---|---|---|
| 2010/0093998 A1 | 4/2010 | Isobe et al. |
| 2011/0077263 A1 | 3/2011 | Kast et al. |
| 2014/0341978 A1 | 11/2014 | Kim et al. |
| 2015/0099770 A1 | 4/2015 | Hori et al. |
| 2017/0114137 A1 | 4/2017 | Li |
| 2017/0216276 A1 | 8/2017 | Vasilakos et al. |
| 2018/0127717 A1 | 5/2018 | Decker et al. |
| 2018/0311505 A1 | 11/2018 | Fisher et al. |

FOREIGN PATENT DOCUMENTS

| | | |
|---|---|---|
| JP | 2015-520729 A | 7/2015 |
| JP | 2017-523244 A | 8/2017 |
| WO | WO 2008/114817 A1 | 9/2008 |
| WO | WO 2013/043647 A1 | 3/2013 |
| WO | WO 2013/172479 A1 | 11/2013 |
| WO | WO 2016/019232 A1 | 2/2016 |
| WO | WO 2016/179475 A1 | 11/2016 |
| WO | WO 2017/079431 A1 | 5/2017 |
| WO | WO 2018/078620 A1 | 5/2018 |

OTHER PUBLICATIONS

Marin-Acevedo et al (Journal of Hematology and Oncology, 2018, vol. 11, 20 pages) (Year: 2018).*
Yuan et al (Cancer Immunol Immunother, 2011, vol. 60, pp. 1137-1146) (Year: 2011).*
Fujimura et al (Case Reports in Oncology, Jan. 4, 2018, vol. 11, pp. 1-5) (Year: 2019).*
Pardoll, Nature Reviews Cancer, 2012, vol. 12, pp. 252-264 (Year: 2012).*
Extended European Search Report from the European Patent Office in European Application No. EP 18 89 3082, dated Dec. 9, 2021 (24 pages).
Mahoney, Kathleen M., et al., "Combination cancer immunotherapy and new immunomodulatory targets", *Nat. Rev Drug Discovery*, vol. 14, pp. 561-584 (24 pages) (Aug. 2015).
Pardoll, Drew M., "The blockade of immune checkpoints in cancer immunotherapy", *Nat. Rev. Cancer*, vol. 12, pp. 252-264 (13 pages) (Apr. 2012).
Mahoney, Kathleen M., et al., "Combination cancer immunotherapy and new immunomodulatory targets", *Nat. Rev Drug Discovery*, vol. 14, pp. 5661-5684 (24 pages) (Aug. 2015).
Singh, Manisha et al., "Effective Innate and Adaptive Antimelanoma Immunity through Localized TLR7/8 Activation", *The Journal of Immunology*, vol. 193, pp. 4722-4731 (11 pages) (Sep. 2014).
Rausch, Johanna et al., "Combined immunotherapy: CTLA-4 blockage potentiates anti-tumor response induced by transcutaneous immunization", *Journal of Dermatological Science*, vol. 87. No. 3, pp. 300-306 (9 pages) (Sep. 2017).
Nishii, Naoto et al., "Systemic administration of a TLR7 agonist attenuates regulatory T cells by dendritic cell modification and overcomes resistance to PD-L1 blockade therapy", *Oncotarget*, vol. 9, No. 17, pp. 13301-13312 (12 pages) (Jan. 27, 2018).
International Search Report in corresponding International Application No. PCT/JP2018/047011, mailed Mar. 19, 2019 (3 pages).
International Preliminary Report on Patentability in corresponding International Application No. PCT/JP2018/047011, issued Jun. 23, 2020 (12 pages).

(Continued)

*Primary Examiner* — Karen A. Canella
(74) *Attorney, Agent, or Firm* — Finnegan, Henderson, Farabow, Garrett & Dunner, LLP

(57) ABSTRACT

The present invention provides an agent for inducing effector memory T cell or an agent for inducing MHC class I for treating or preventing a cancer, comprising a TLR7 agonist which is used with an immune checkpoint inhibitor. And, the present invention also provides a medicament for treating or preventing a cancer, comprising a TLR7 agonist which is used with an immune checkpoint inhibitor.

33 Claims, 5 Drawing Sheets

(56) References Cited

OTHER PUBLICATIONS

Dyck, Lydia et al., "Anti-PD-1 inhibits Foxp3+ Treg cell conversion and unleashes intratumoural effector T cells thereby enhancing the efficacy of a cancer vaccine in a mouse model", *Cancer Immunol Immunother*, 65:1491-1498 (8 pages) (Dec. 2016).

Joseph, Richard W. et al., "Treatment of in-transit and metastatic melanoma in two patients treated with ipilimumab and topical imiquimod", *Melanoma Research*, 26(4): 409-12 (4 pages) (Aug. 2016).

Naoto Nishii et al., "Combined Treatment With PD-L1 Blockade and a TLR7/8 Agonist Dramaticallly Enhances Antitumor Immunity", *Cancer Research* vol. 76, No. 14, Abstract No. 563 (2 pages) (2016).

Fumi Sato-Kaneko et al., "Immunotherapy of head and neck squamous cell cancers with synthetic TLR agonists and checkpoint inhibitors in preclinical models", *Journal for ImmunoTherapy of Cancer*, 4(Suppl 1):73 (1 page) (2016).

Xu, Jun et al., "Near-Infrared-Triggered Photodynamic Therapy with Multitasking Upconversion Nanoparticles in Combination with Checkpoint Blockade for Immunotherapy of Colorectal Cancer", *ACS Nano*, 11(5):4463-4474 (12 pages) (Mar. 31, 2017).

Chen, Qian et al., "Photothermal therapy with immune-adjuvant nanoparticles together with checkpoint blockade for effective cancer immunotherapy", *Nature Communications*, 7:13193 (13 pages) (Oct. 21, 2016).

Carson, Dennis et al.: "Application of novel phospholipid conjugated Toll like receptor 7 ligands for cancer therapy by topical and systemic administration", *Cancer Research*, vol. 74, No. 19, Abstract No. 2568 (2 pages) (Apr. 2014).

*Cancer Research*, vol. 73 (24 Suppl) Abstract No. P5-01-06 (2 pages) (2013).

Nishii, Naoto et al., "Antitumor effects of a low dose systemic administration of a TLR7/8 agonist and its combined therapy with PD-L1 blockade", Annual Meeting of the Japanese Society for Immunology (JSI) 2016, p. 136 (1 page).

Popivanova, Boryana K. et al., "Anti-tumor activity of TLR7 stimulation through enhanced anti-tumor CTL induction," Annual Meeting of the Japanese Society for Immunology (JSI) 2012, p. 173 (1 page).

Supplement slides used in Annual Meeting of the Japanese Society for Immunology (JSI) 2012, p. 173 (17 pages).

Supplementary Partial European Search Report from the European Patent Office dated Aug. 13, 2021, in European Application No. EP 18893082, 23 pages.

Fumi Sato-Kaneko et al., "Combination immunotherapy with TLR agonists and checkpoint inhibitors suppresses head and neck cancer", JCI Insight, vol. 2, No. 18, Sep. 21, 2017, pp. 1-18.

Andrea Khong et al., "The efficacy of tumor debulking surgery is improved by adjuvant immunotherapy using imiquimod and anti-CD40", BMC Cancer, Biomed Central, London, vol. 14, No. 1, Dec. 17, 2014, pp. 1-9.

Steve A. Bloomfield et al., "Locally Administered TLR7 Agonists Drive Systemic Antitumor Immune Responses That Are Enhanced by Anti-CD40 Immunotherapy", The Journal of Immunology, Williams & Wilkins Co., US, vol. 182, No. 9, May 1, 2009, pp. 5217-5224.

Anonymous: "CD40 & DC40L Immune Checkpoint Pathway : Sino Biological", Jan. 1, 2021, Retrieved from the Internet: https://www.sinobiological.com/research/immune-checkpoint/cd40-cd40l-pathway [retrieved on Aug. 9, 2021], 4 pages.

Kharkeyvich, D. A., "Pharmacology," Manual for High Schools, Tenth Edition, GEOTAR-Media, Moscow, Russia, (2010), 27 pages.

Mashkovsky, M. D., "Drugs," Manual for Physicians, vol. 1, Fourteenth Edition, Novaya Volna: S.B. Divov, Moscow, Russia, (2001), 7 pages.

Tallarida, R. J. et al., "Quantitative Methods for Assessing Drug Synergism," Genes & Cancer, vol. 2, No. 11, (2011), pp. 1003-1008.

Vengerovsky, A. I., "Pharmacological incompatibility," Bulletin of Siberian Medicine, Siberian State Medical University—Tomsk, Russia, (2003), 18 pages.

\* cited by examiner

Engraftment after re-transferred tumor

|  | Number of therapeutically-responsible subjects | Number of engraftment-acceptable subject after re-transfer |
|---|---|---|
| Compound 1 | 1／8 | 0／1 |
| Anti-PD-1 antibody | 1／8 | 1／1 |
| Anti-PD-1 antibody + Compound 1 | 6／8 | 0／6 |

COMBINATION DRUG INCLUDING TLR7 AGONIST

This is a national stage application under 35 U.S.C. § 371 of International Patent Application No. PCT/JP2018/047011, filed Dec. 20, 2018, which claims the benefit of Japanese Patent Application No. 2017-244675, filed Dec. 21, 2017, both of which are incorporated herein by reference.

TECHNICAL FIELD

The present invention relates to a combination of a TLR7 agonist and an immune checkpoint inhibitor.

BACKGROUND ART

As one of receptors involved in xenobiotic recognition for virus, microorganism, etc., Toll-like receptors (TLRs) have been known. TLRs are a kind of pattern recognition receptors (PRRs) since they can recognize the pattern of virus or bacteria. Until now, 10 kinds of subtypes thereof have been found in human beings. It has become clear that each subtype of TLRs recognizes different ligands, for example, these subtypes recognize lipopolysaccharide (LPS) on bacterial surface, lipoprotein, flagellin, viral double-stranded RNA, or unmethylated CpG island which is contained in bacterial DNA or viral DNA.

When TLRs are activated, the activated TLRs activate innate immunity through humoral factor such as cytokine to eliminate xenobiotic. In order to eliminate cancer cells, cell-mediated immunity, especially cytotoxic T-lymphocyte (referred to as "CTL") plays an important function. The CTL is produced by differentiation and proliferation of a precursor T cell recognizing a complex of an antigen peptide on cancer cells (cancer antigen peptide) and MHC (Major Histocompatibility Complex) class I, and the produced CTL attacks cancer cells.

TLR7 is highly expressed in endosome, compared with other members of the TLR family, which can recognize mainly single-stranded RNA derived from virus. TLR7 is highly expressed in immune cells, especially plasmacytoid dendritic cell (pDC). When stimulating TLR7 in pDC, mainly interferon α which is type I interferon is secreted. When TLR7 is activated, MYD88 assembles and thereby signal cascade is initiated. And, the transcription of many immunological factors is activated by NF-κB or IRF7 which is a transcription factor. Interferon α is a kind of cytokines, which has antiviral activity and antitumor activity, and Interferon α is a cytokine which has been in practical use for treating HCV and HBC, as well as cancer.

When TLR is stimulated, antigen-presenting cells including dendritic cells internalize an antigen derived from a cancer cell and then enhance the antigen-recognition ability of CD8-positive T-cell to activate the CTL induction. The activated CTL recognizes the tumor, and exerts an antitumor effect to the tumor through cytotoxicity action or cytokine production.

For example, imiquimod which is a TLR7 and TLR8 agonist has been in practical use as a medicament for treating basal cell carcinoma. As other TLR7 agonists, TLR7 and TLR8 agonists such as resiquimod (R848), MEDI-9197, and PF-4878691 (852A) have been reported. Furthermore, as a TLR7 agonist, imiquimod, loxoribine, and the compounds disclosed in Patent Literature 1 have been reported.

Even though CTL exists in the vicinity of a cancer, the cancer cannot sometimes be reduced or disappeared. As one of the causes, it is suggested that CTL in the vicinity of a tumor can get early exhausted; and the cytotoxicity against cancer cells can disappear, and the productive/proliferative capacity of plural cytokines can disappear, and consequently CTL goes into cell death. It has been clarified that the exhaustion is caused by a negative signal coming from an immune checkpoint molecule expressed on the surface of cell membrane of CTL.

Until now, CTLA-4, PD-1, PD-L1, PD-L2, LAG-3, KIR, TIM-3, B7-H3, B7-H4, VISTA/PD-1H, HVEM, BTLA, CD160, GAL9, TIGIT, PVR, BTNL2, BTN1A1, BTN2A2, BTN3A2, CSF-1R, etc. have been reported as immune checkpoint molecule (Non-patent Literature 1). For example, PD-1 is a receptor classified as CD28 family expressed on activated lymphocyte (T cell, B cell, and NKT cell) and myeloid cell, and is connected to PD-1 ligands (PD-L1 and PD-L2) expressed in antigen-presenting cells to transmit an inhibitory signal to lymphocyte and consequently regulate the active mode of lymphocyte to negative one. It has been clarified that PD-L1 is also expressed in various cancer cells besides antigen-presenting cells, i.e., cancers can evade the attack from CTL through PD-L1.

Recently, the development for antibodies which can inhibit the function of immune checkpoint molecules has started (Non-patent Literature 2). These antibodies can recover the exhaustion state of CTL. For example, an anti-PD-1 antibody or an anti-PD-L1 antibody can inhibit the binding of PD-1 and PD-L1 to recover the cytotoxicity activity of CTL. Actually, clinical tests of an anti-PD-1 antibody or an anti-PD-L1 antibody for patients suffering from non-small-cell lung cancer or melanoma have been carried out, and some patients have obtained prominent effect. However, it is only about 20 to 30% in all cases that such prominent effect brought in patients, and some patients experienced severe immune-related adverse event. That is, the therapeutic method using anti-PD-1 antibody or anti-PD-L1 antibody has been insufficient yet.

Recently, it has been reported that the combination of anti-PD-1 antibody or anti-PD-L1 antibody, and MEDI-9197 which is known as TLR7 and TLR8 agonists can enhance the antitumor immune activity of anti-PD-1 antibody/anti-PD-L1 antibody (Non-patent Literature 3).

PRIOR ART

Patent Reference

[Patent Literature 1] WO 2013/172479

Non-Patent Reference

[Non-patent Literature 1] Nat Rev Cancer. 2012; 12: 252-64
[Non-patent Literature 2] Nat Rev Drug Discov. 2015 August; 14 (8): 561-8
[Non-patent Literature 3] J Immunol. 2014 Nov. 1; 193 (9):4722-31

SUMMARY OF INVENTION

Technical Problem

The purpose of the present invention may be to provide a drug for treating or preventing a cancer, which is characterized by a long-term immune-inducing activity. In addition, the purpose of the present invention may be also to provide a drug for treating or preventing a cancer, which is characterized in that the drug can show efficacy in a patient having refractoriness to immune checkpoint inhibitors or a patient with recurrent episodes of cancer.

Solution to Problem

The present inventors have extensively studied, and then they have found that MHC class I expression in cancer cells can be increased by using an immune checkpoint inhibitor and a TLR7 agonist in combination, and the anticancer activity of the combination is more potent than using each agent alone. In addition, the present inventors have also found that the above combination can increase effector memory T cell in lymphocyte which infiltrates in tumor to maintain a long-term anticancer immunity and can block the engraftment of tumor re-transplantation. Based upon the findings, the present invention has been completed.

Accordingly, the present invention is described as follows:

(Item 1) An agent for inducing effector memory T cell, comprising a TLR7 agonist, which is used in combination with an immune checkpoint inhibitor.

(Item 2) An agent for inducing MHC class I, comprising a TLR7 agonist, which is used in combination with an immune checkpoint inhibitor.

(Item 3) The agent of Item 1 or 2, which is for treating a cancer or an infection.

(Item 4) The agent of Item 1 or 2, which is for treating a cancer.

(Item 5) The agent of Item 3 or 4, wherein the cancer is selected from the group consisting of non-small-cell lung cancer; small cell lung cancer; pancreatic cancer; malignant melanoma; renal cell carcinoma; gastric cancer; colon cancer; rectal cancer; small intestinal cancer; breast cancer; germ cell cancer; bladder cancer; prostate cancer; endometrial cancer; cervical cancer; ovarian cancer; liver cancer; Merkel cell carcinoma; bone cancer; head and neck cancer; cutaneous or intraorbital malignant melanoma; anal cancer; testicular cancer; esophageal cancer; endocrine system cancer; thyroid cancer; parathyroid cancer; adrenal cancer; soft tissue sarcoma; urothelial cancer; penile cancer; glioblastoma multiforme; brain tumor; chronic or acute leukemia including acute myeloid leukemia, chronic myeloid leukemia, acute lymphoblastic leukemia, and chronic lymphocytic leukemia; malignant lymphoma including Hodgkin's lymphoma and non-Hodgkin's lymphoma; myelodysplastic syndrome; and multiple myeloma.

(Item 6) The agent of any one of Items 1 to 5, which is administered to a patient having refractoriness to an immune checkpoint inhibitor.

(Item 7) The agent of any one of Items 1 to 6, which is administered to a patient who has relapsed with a cancer.

(Item 8) The agent of any one of Items 1 to 7, which has a long-term anticancer immunity.

(Item 9) The agent of any one of Items 1 to 8, wherein the TLR7 agonist is a compound having a pyrimidine skeleton, an adenine skeleton, an imidazoquinoline skeleton, a guanine skeleton, or a dihydropteridine skeleton; or a pharmaceutically acceptable salt thereof.

(Item 10) The agent of Item 9, wherein the TLR7 agonist is a compound having a pyrimidine skeleton, an adenine skeleton, or an imidazoquinoline skeleton; or a pharmaceutically acceptable salt thereof.

(Item 11) The agent of any one of Items 1 to 8, wherein the TLR7 agonist is imiquimod, loxoribine, or any one of the following compounds:

N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, 6-amino-2-(butylamino)-9-({6-[2-(dimethylamino)ethoxy]pyridin-3-yl}methyl)-7,9-dihydro-8H-purin-8-one, 6-amino-9-({6-[2-(dimethylamino)ethoxy]pyridin-3-yl}methyl)-2-ethoxy-7,9-dihydro-8H-purin-8-one, and N-(4-{[6-amino-2-(butylamino)-8-oxo-7,8-dihydro-9H-purin-9-yl]methyl}benzoyl)glycine, or a pharmaceutically acceptable salt thereof.

(Item 12) The agent of Item 11, wherein the TLR7 agonist is any one of the following compounds:

N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, 6-amino-2-(butylamino)-9-({6-[2-(dimethylamino)ethoxy]pyridin-3-yl}methyl)-7,9-dihydro-8H-purin-8-one, and 6-amino-9-({6-[2-(dimethylamino)ethoxy]pyridin-3-yl}methyl)-2-ethoxy-7,9-dihydro-8H-purin-8-one, or a pharmaceutically acceptable salt thereof.

(Item 13) The agent of Item 12, wherein the TLR7 agonist is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof.

(Item 14) The agent of any one of Items 1 to 13, wherein the immune checkpoint inhibitor is at least one medicament that can inhibit the function of a molecular which is selected from the group consisting of
(1) CTLA-4,
(2) PD-1,
(3) LAG-3,
(4) BTLA,
(5) KIR,
(6) TIM-3,
(7) PD-L1,
(8) PD-L2,
(9) B7-H3,
(10) B7-H4,
(11) HVEM,
(12) GAL9,
(13) CD160,
(14) VISTA,
(15) BTNL2,
(16) TIGIT,
(17) PVR,
(18) BTN1A1,
(19) BTN2A2,
(20) BTN3A2, and
(21) CSF-1R.

(Item 15) The agent of Item 14, wherein the immune checkpoint inhibitor is at least one medicament that can inhibit the function of a molecular which is selected from the group consisting of CTLA-4, PD-1, LAG-3, TIM-3, BTLA, VISTA, HVEM, TIGIT, PVR, PD-L1, and CD160.

(Item 16) The agent of Item 14, wherein the immune checkpoint inhibitor is at least one medicament which can inhibit the function of a molecular which is selected from the group consisting of PD-1, LAG-3, TIM-3, BTLA, VISTA, HVEM, TIGIT, PVR, PD-L1, and CD160.

(Item 17) The agent of Item 14, wherein the immune checkpoint inhibitor is a medicament which can inhibit the function of a molecular of PD-1 or PD-L1.

(Item 18) The agent of any one of Items 14 to 17, wherein the immune checkpoint inhibitor is an antibody against the molecular.

(Item 19) The agent of Item 18, wherein the immune checkpoint inhibitor is anti-PD-1 antibody, anti-PD-L1 antibody, or anti-CTLA-4 antibody.

(Item 20) The agent of Item 18, wherein the immune checkpoint inhibitor is anti-PD-1 antibody or anti-PD-L1 antibody.

(Item 21) The agent of Item 19 or 20, wherein the anti-PD-1 antibody is nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, or BCD-100.

(Item 22) The agent of Item 19 or 20, wherein the anti-PD-L1 antibody is durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, or BMS-936559.

(Item 23) The agent of Item 18, wherein the immune checkpoint inhibitor is anti-CTLA-4 antibody.

(Item 24) The agent of Item 19 or 23, wherein the anti-CTLA-4 antibody is ipilimumab, tremelimumab, BMS-986218, MK-1308, ADU-1604, BMS-986249, CS-1002, BCD-145, or REGN-4659.

(Item 25) The agent of any one of Items 1 to 24, wherein the TLR7 agonist and the immune checkpoint inhibitor are simultaneously administered.

(Item 26) The agent of any one of Items 1 to 24, wherein the TLR7 agonist and the immune checkpoint inhibitor are separately administered.

(Item 27) The agent of any one of Items 1 to 24, wherein the TLR7 agonist is administered prior to the immune checkpoint inhibitor.

(Item 28) The agent of any one of Items 1 to 24, wherein the TLR7 agonist is administered posterior to the immune checkpoint inhibitor.

(Item 29) The agent of any one of Items 1 to 28, further comprising a pharmaceutically acceptable carrier.

(Item 30) A kit of an agent for inducing effector memory T cell, comprising a TLR7 agonist and an immune checkpoint inhibitor.

(Item 31) A kit of an agent for inducing MHC class I, comprising a TLR7 agonist and an immune checkpoint inhibitor.

(Item 32) A method for inducing effector memory T cell or inducing MHC class I, which comprises administering a therapeutically effective amount of a TLR7 agonist and a therapeutically effective amount of an immune checkpoint inhibitor to a mammal.

(Item 33) A TLR7 agonist in use for inducing effector memory T cell or inducing MHC class I, which is used with an immune checkpoint inhibitor.

(Item 34) An immune checkpoint inhibitor in use for inducing effector memory T cell or inducing MHC class I, which is used with a TLR7 agonist.

(Item 35) Use of a TLR7 agonist in manufacture of a medicament for inducing effector memory T cell or inducing MHC class I, which is used with an immune checkpoint inhibitor.

(Item 36) Use of an immune checkpoint inhibitor in manufacture of a medicament for inducing effector memory T cell or inducing MHC class I, which is used with a TLR7 agonist.

(Item 37) Use of a TLR7 agonist and an immune checkpoint inhibitor in manufacture of a medicament for inducing effector memory T cell or inducing MHC class I.

(Item 38) An agent for treating or preventing a cancer, comprising N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof, which is used with an immune checkpoint inhibitor.

(Item 39) The agent of Item 38, wherein the immune checkpoint inhibitor is anti-PD-1 antibody, anti-PD-L1 antibody, or anti-CTLA-4 antibody.

(Item 40) The agent of Item 38, wherein the immune checkpoint inhibitor is anti-PD-1 antibody or anti-PD-L1 antibody.

(Item 41) The agent of Item 38, wherein the immune checkpoint inhibitor is anti-CTLA-4 antibody.

(Item 42) The agent of Item 39 or 40, wherein the anti-PD-1 antibody is nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, or BCD-100.

(Item 43) The agent of Item 39 or 40, wherein the anti-PD-L1 antibody is durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, or BMS-936559.

(Item 44) The agent of Item 39 or 41, wherein the anti-CTLA-4 antibody is ipilimumab, tremelimumab, BMS-986218, MK-1308, ADU-1604, BMS-986249, CS-1002, BCD-145, or REGN-4659.

(Item 45) The agent of any one of Items 38 to 44, which is administered to a patient who is resistant to an immune checkpoint inhibitors.

(Item 46) The agent of any one of Items 38 to 44, which is administered to a patient who suffers relapse of a cancer.

(Item 47) The agent of any one of Items 38 to 44, which has a long-term anticancer immunity.

(Item 48) The agent of any one of Items 38 to 44, wherein N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof and,
an immune checkpoint inhibitor
are simultaneously or separately administered.

(Item 49) The agent of any one of Items 38 to 44, wherein N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof is administered prior to or posterior to the immune checkpoint inhibitor.

(Item 50) The agent of any one of Items 38 to 44, further comprising a pharmaceutically acceptable carrier.

(Item 51) A kit of an agent for treating or preventing a cancer, comprising N-{4-[(2-amino-4-{[(3S)-1-hydroxyhexan-3-yl]amino}-6-methylpyrimidin-5-yl) methyl]-3-methoxybenzyl}-N-(2,2,2-trifluoroethyl) glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof, and an immune checkpoint inhibitor.

(Item 52) A method for treating or preventing a cancer, which comprises administering a therapeutically effective amount of a TLR7 agonist and a therapeutically effective amount of an immune checkpoint inhibitor to a mammal.

(Item 53) A TLR7 agonist in use for treating or preventing a cancer, which is used with an immune checkpoint inhibitor.

(Item 54) An immune checkpoint inhibitor in use for treating or preventing a cancer, which is used with a TLR7 agonist.

(Item 55) Use of a TLR7 agonist in manufacture of a medicament for treating or preventing a cancer, which is used with an immune checkpoint inhibitor.

(Item 56) Use of an immune checkpoint inhibitor in manufacture of a medicament for treating or preventing a cancer, which is used with a TLR7 agonist.

(Item 57) Use of a TLR7 agonist and an immune checkpoint inhibitor in manufacture of a medicament for treating or preventing a cancer.

(Item 58) The method of Item 52, the agent of Item 53 or 54, or the use of any one of Items 55 to 57, wherein the TLR7 agonist is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl] amino}-6-methylpyrimidin-5-yl)methyl]-3-methoxybenzyl}-N-(2,2-difluoroethyl)glycine, or a pharmaceutically acceptable salt thereof.

Effect of the Invention

The present invention provides
an agent for inducing effector memory T cell or an agent for inducing MHC class I, wherein a TLR7 agonist and an immune checkpoint inhibitor are used together,
a medicament comprising a TLR7 agonist which is used with an immune checkpoint inhibitor, and
a kit of an agent for inducing effector memory T cell or an agent for inducing MHC class I, comprising a TLR7 agonist and an immune checkpoint inhibitor,
and etc.

DESCRIPTION OF EMBODIMENTS

Figure 1:
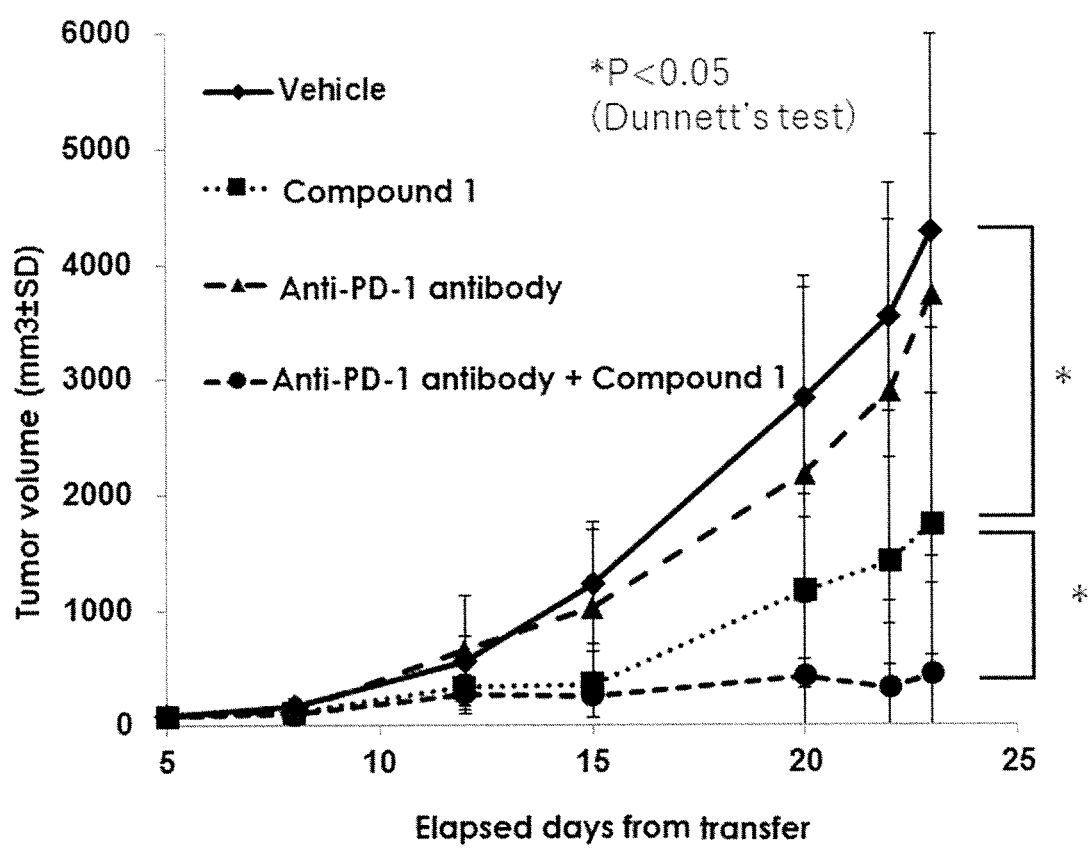
FIG. 1 shows tumor growth curves of each administration group. The ordinate denotes tumor volume, and the abscissa denotes elapsed days from the transplantation of the tumor cell.

Hereinafter, the embodiments of the present invention are explained in detail.

The TLR7 agonist used herein, which enhances the bioactivity of TLR7, i.e., which has TLR7 receptor agonist activity, means a compound enhancing TLR7 receptor function, but not limited thereto.

The TLR7 agonist used herein is preferably a low-molecular-weight compound, for example, whose molecular weight is 200-600, preferably 250-500, more preferably 300-500.

The TLR7 agonist used herein includes preferably a TLR7-selective agonist. The "TLR7-selective" herein means that the agonist-activities of TLR receptors other than TLR7 receptor are lower than that of TLR7 receptor. For example, it may be exemplified by a case wherein TLR7 receptor agonist activity is more potent than TLR8 receptor agonist activity which takes single-stranded RNA as an endogenous ligand, in more detail, a case wherein the TLR7 receptor agonist activity ($EC_{50}$ value) is 30 or more times as potent as that of a TLR8 receptor.

The TLR7 agonist used herein includes preferably a compound having an adenine skeleton, a pyrimidine skeleton, an imidazoquinoline skeleton, a guanine skeleton, or a dihydropteridine skeleton, more preferably, a compound having an adenine skeleton, a pyrimidine skeleton, or an imidazoquinoline skeleton.

The compound having an adenine skeleton includes a compound having a 4-amino-8-oxo-purine (8-oxoadenine) skeleton, for example, a compound having a 4-amino-8-oxo-purine skeleton whose 9th position is substituted with an alkyl group (for example, linear $C_{1-6}$ alkyl group) which may be substituted with 5- to 6-membered aromatic carbocyclyl, 5- to 6-membered aromatic heterocyclyl, or 4- to 7-membered aliphatic nitrogen-containing heterocyclyl. For example, it includes GSK-2245035 (6-amino-2-{[(1S)-1-methylbutyl]oxy}-9-[5-(1-piperidinyl)pentyl]-7,9-dihydro-8H-purin-8-one), PF-4171455 (4-amino-1-benzyl-6-trifluoromethyl-1,3-dihydroimdazo[4,5-c]pyridin-2-one), etc. which are disclosed in MedChemComm 2011, 2, 185; or compounds disclosed in WO 1998/01448, WO 1999/28321, WO 2002/085905, WO 2008/114008, WO 2008/114819, WO 2008/114817, WO 2008/114006, WO 2010/018131, WO 2010/018134, WO 2008/101867, WO 2010/018133, WO 2009/005687, etc. The compound having an adenine skeleton includes preferably 6-amino-9-({6-[2-(dimethylamino)ethoxy]pyridin-3-yl}methyl)-2-ethoxy-7,9-dihydro-8H-purin-8-one, 6-amino-2-(butylamino)-9-({6-[2-(dimethylamino)ethoxy]pyridin-3-yl}methyl)-7,9-dihydro-8H- purin-8-one, and CL264 (N-(4-{[6-amino-2-(butylamino)-8-oxo-7,8-dihydro-9H-purin-9-yl]methyl}benzoyl)glycine).

The compound having a pyrimidine skeleton includes a compound having a 2,4-diaminopyrimidine skeleton, for example, a compound having a 2,4-diaminopyrimidine whose 6th position is substituted with an alkyl group and whose 5th position is substituted with an alkyl group (for example, linear $C_{1-6}$ alkyl group) which may be substituted with 5- to 6-membered aromatic carbocyclyl, 5- to 6-membered aromatic heterocyclyl, or 4- to 7-membered aliphatic nitrogen-containing heterocyclyl. It may include, for example, some compounds disclosed in WO 2000/12487, WO 2010/133885, WO 2013/172479, and WO 2012/136834. Preferred compounds having a pyrimidine skeleton includes N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine (Patent Literature 1, Example 4, Formula (I) shown below), N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine (Patent Literature 1, Example 3, Formula (II) shown below).

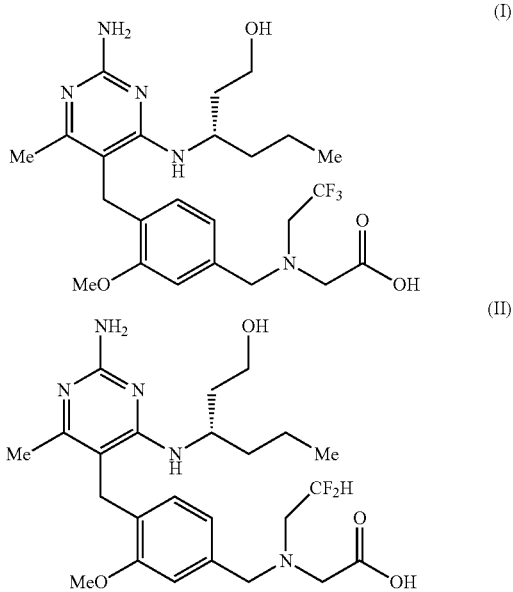

The compound having an imidazoquinoline skeleton includes a compound having a 4-amino-1H-imidazo[4,5-c]quinoline skeleton such as imiquimod, resiquimod, and 852A (N-[4-(4-amino-2-ethyl-1H-imidazo[4,5-c]quinolin-1-yl)butyl]methanesulfonamide), and for example, 4-amino-1H-imidazo[4,5-c]quinoline whose 1st position is substituted with $C_{1-6}$ alkyl group or $C_{1-6}$ alkoxy group, and whose 2nd position is substituted with $C_{1-6}$ alkyl group or $C_{1-6}$ alkoxy group. It may include, for example, some compounds disclosed in WO 2010/48520, WO 2008/135791, U.S. Pat. Nos. 4,689,338, 4,698,348, and WO 2007/030777.

The compound having an imidazoquinoline skeleton includes preferably imiquimod.

The compound having a guanine skeleton includes a compound having a 2-amino-6-oxopurine skeleton, for example loxoribine.

The compound having a dihydropteridine skeleton includes a compound having a 4-amino-7,8-dihydropteridin-6(5H)-one skeleton, for example, vesatolimod (4-amino-2-butoxy-8-[[3-[(pyrrolidin-1-yl)methyl]phenyl]methyl]-7,8-dihydropteridin-6(5H)-one).

In addition, the low-molecular-weight compound as a TLR7 agonist may include isatoribine, ANA-773, and some compounds disclosed in WO 2010/077613.

The "immune checkpoint inhibitor" used herein means a substance which can inhibit immunosuppression caused by cancer cells or antigen-presenting cells. The immune checkpoint inhibitor includes a drug which can inhibit the function of a molecule that has been reported to act as an immune inhibitor, but not limited thereto, for example, the following compounds which have been reported to act as an immune inhibitor: (1) CTLA-4 (such as ipilimumab, tremelimumab, BMS-986218, MK-1308, ADU-1604, BMS-986249, CS-1002, BCD-145, and REGN-4659); (2) PD-1 (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100); (3) PD-L1 (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and BMS-936559); (4) PD-L2; (5) LAG-3 (such as IMP-321 and BMS-986016); (6) KIR (such as IPH2101); (7) TIM-3; (8) B7-H3 (such as MGA-271); (9) B7-H4; (10) VISTA; (11) HVEM; (12) BTLA; (13) CD160; (14) GAL9; (15) TIGIT; (16) PVR; (17) BTNL2; (18) BTN1A1; (19) BTN2A2; (20) BTN3A2 (Nat Rev Drug Discov. 2013; 12: 130-146; Nikkei Medical Cancer Review 2014; 9; Nat Rev Immunol. 2014; 14: 559-69); and (21) CSF1-R.

The immune checkpoint inhibitor includes preferably a medicament which can inhibit the function of CTLA-4, PD-1, PD-L1, LAG-3, TIM-3, VISTA, HVEM, BTLA, CD160, TIGIT, or PVR, more preferably a medicament which can inhibit the function of CTLA-4, PD-1, or PD-L1.

The immune checkpoint inhibitor also includes preferably an antibody against the above-mentioned molecular, for example, anti-CTLA-4 antibody, anti-PD-1 antibody, anti-PD-L1 antibody, anti-LAG-3 antibody, anti-TIM-3 antibody, anti-VISTA antibody, anti-HVEM antibody, anti-BTLA antibody, anti-CD160 antibody, anti-TIGIT antibody, or anti-PVR antibody.

The anti-CTLA-4 antibody is a protein recognizing CTLA-4 molecule, which has Y-like quadruple-stranded structure (each two of two polypeptide chains of light strand and heavy strand), and which selectively recognizes one molecule with its fragment antigen binding site (hereinafter, referred to as "Fab site"). The anti-CTLA-4 antibody may be prepared by cell-fusing B cell which produces antibody and myeloma to prepare hybridoma, and then purifying the antibody secreted in the culture supernatant.

The anti-PD-1 antibody is a protein recognizing PD-1 molecule, which has Y-like quadruple-stranded structure (each two of two polypeptide chains of light strand and heavy strand), and which selectively recognizes one molecule with the Fab site. The anti-PD-1 antibody may be prepared by cell-fusing B cell which produces antibody and myeloma to prepare hybridoma, and then purifying the antibody secreted in the culture supernatant.

The anti-PD-L1 antibody is a protein recognizing PD-L1, which has Y-like quadruple-stranded structure (each two of two polypeptide chains of light strand and heavy strand), and which selectively recognizes one molecule with the Fab site. The anti-PD-L1 antibody may be prepared by cell-fusing B cell which produces antibody and myeloma to prepare hybridoma, and then purifying the antibody secreted in the culture supernatant.

In the same way, the anti-LAG-3 antibody, anti-TIM-3 antibody, anti-VISTA antibody, anti-HVEM antibody, anti-BTLA antibody, anti-CD160 antibody, anti-TIGIT antibody, or anti-PVR antibody is a protein recognizing each molecule, which has Y-like quadruple-stranded structure (each two of two polypeptide chains of light strand and heavy strand), and which selectively recognizes one molecule. These antibodies may be prepared by cell-fusing B cell which produces each antibody and myeloma to prepare hybridoma, and then purifying each antibody secreted in the culture supernatant.

For example, the antibody which is an immune checkpoint inhibitor includes preferably an anti-CTLA-4 antibody (such as ipilimumab, tremelimumab, BMS-986218, MK-1308, ADU-1604, BMS-986249, CS-1002, BCD-145, and REGN-4659), an anti-PD-1 antibody (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100), an anti-PD-L1 antibody (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and BMS-936559), an anti-LAG-3 antibody (such as IMP-321 and BMS-986016), an anti-TIM-3 antibody, an anti-VISTA antibody, an anti-HVEM antibody, an anti-BTLA antibody, an anti-CD160 antibody, an anti-TIGIT antibody, and an anti-PVR antibody. More preferably, it includes an anti-CTLA-4 antibody (such as ipilimumab, tremelimumab, BMS-986218, MK-1308, ADU-1604, BMS-986249, CS-1002, BCD-145, and REGN-4659), an anti-PD-1 antibody (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100), and an anti-PD-L1 antibody (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and BMS-936559). Particularly preferably, it includes an anti-CTLA-4 antibody (ipilimumab, tremelimumab), an anti-PD-1 antibody (nivolumab, pembrolizumab, cemiplimab, tislelizumab, dostarlimab, spartalizumab, camrelizumab, genolimzumab, sintilimab), and an anti-PD-L1 antibody (durvalumab, atezolizumab, avelumab).

As the agent for inducing effector memory T cell or the agent for inducing MHC class I used herein, One embodiment of the combination of a TLR7 agonist and an immune checkpoint inhibitor includes a combination of a TLR7 agonist with medicament(s) that can inhibit the function of a molecular which is selected from the group consisting of: (1) CTLA-4; (2) PD-1; (3) PD-L1; (4) PD-L2; (5) LAG-3; (6) KIR; (7) TIM-3; (8) B7-H3; (9) B7-H4; (10) VISTA; (11) HVEM; (12) BTLA; (13) CD160; (14) GAL9; (15) TIGIT; (16) PVR; (17) BTNL2; (18) BTN1A1; (19) BTN2A2; (20) BTN3A2; and (21) CSF1-R.

Another embodiment of the combination of a TLR7 agonist and an immune checkpoint inhibitor includes a combination of a TLR7-selective agonist with a medicament that can inhibit the function of a molecular which is selected from the group consisting of: CTLA-4; PD-1; PD-L1; LAG-3; TIM-3; VISTA; HVEM; BTLA; CD160; TIGIT; and PVR.

Another embodiment of the combination of a TLR7 agonist and an immune checkpoint inhibitor includes a combination of a TLR7-selective agonist which has an adenine skeleton, a pyrimidine skeleton, an imidazoquinoline skeleton, a guanine skeleton, or a dihydropteridine skeleton; and a medicament that can inhibit the function of a molecular which is selected from the group consisting of: CTLA-4; PD-1; PD-L1; LAG-3; TIM-3; VISTA; HVEM; BTLA; CD160; TIGIT; and PVR.

Another embodiment of the combination of a TLR7 agonist and an immune checkpoint inhibitor includes a combination of a TLR7-selective agonist which has an adenine skeleton, a pyrimidine skeleton, or an imidazoquinoline skeleton; and an antibody which is selected from the group consisting of: an anti-CTLA-4 antibody (such as ipilimumab, tremelimumab, BMS-986218, MK-1308, ADU-1604, BMS-986249, CS-1002, BCD-145, and REGN-4659); an anti-PD-1 antibody (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100); an anti-PD-L1 antibody (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and BMS-936559); an anti-LAG-3 antibody (such as IMP-321 and BMS-986016); an anti-TIM-3 antibody; an anti-VISTA antibody; an anti-HVEM antibody; an anti-BTLA antibody; an anti-CD160 antibody; an anti-TIGIT antibody; and an anti-PVR antibody.

Another embodiment of the combination of a TLR7 agonist and an immune checkpoint inhibitor includes a combination of a TLR7-selective agonist which is selected from the group consisting of: imiquimod; loxoribine; N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine; N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine; 6-amino-2-(butylamino)-9-({6-[2-(dimethylamino)ethoxy]pyridin-3-yl}methyl)-7,9-dihydro-8H-purin-8-one; 6-amino-9-({6-[2-(dimethylamino)ethoxy]pyridin-3-yl}methyl)-2-ethoxy-7,9-dihydro-8H-purin-8-one; N-(4-{[6-amino-2-(butylamino)-8-oxo-7,8-dihydro-9H-purin-9-yl]methyl}benzoyl)glycine (CL264), and a pharmaceutically acceptable salt thereof; and an antibody which is selected from the group consisting of: an anti-CTLA-4 antibody (such as ipilimumab, tremelimumab, BMS-986218, MK-1308, ADU-1604, BMS-986249, CS-1002, BCD-145, and REGN-4659); an anti-PD-1 antibody (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100); and an anti-PD-L1 antibody (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and BMS-936559).

Another embodiment of the combination of a TLR7 agonist and an immune checkpoint inhibitor includes a combination of a TLR7-selective agonist which is selected from the group consisting of: N-{4-[(2-amino-4-{[(3S)-1-hydroxyhexan-3-yl]amino}-6-methylpyrimidin-5-yl)

methyl]-3-methoxybenzyl}-N-(2,2,2-trifluoroethyl)glycine; N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine; 6-amino-2-(butylamino)-9-({6-[2-(dimethylamino)ethoxy]pyridin-3-yl}methyl)-7,9-dihydro-8H-purin-8-one; 6-amino-9-({6-[2-(dimethylamino)ethoxy]pyridin-3-yl}methyl)-2-ethoxy-7,9-dihydro-8H-purin-8-one, and a pharmaceutically acceptable salt thereof; and an antibody which is selected from the group consisting of: an anti-CTLA-4 antibody (such as ipilimumab, tremelimumab, BMS-986218, MK-1308, ADU-1604, BMS-986249, CS-1002, BCD-145, and REGN-4659); an anti-PD-1 antibody (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100); and an anti-PD-L1 antibody (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and BMS-936559).

Another embodiment of the combination of a TLR7 agonist and an immune checkpoint inhibitor includes a combination of a TLR7-selective agonist which is selected from the group consisting of: N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine; N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, and a pharmaceutically acceptable salt thereof; and an antibody which is selected from the group consisting of: an anti-PD-1 antibody (such as nivolumab, pembrolizumab, cemiplimab, tislelizumab, dostarlimab, spartalizumab, camrelizumab, genolimzumab, and sintilimab); an anti-CTLA-4 antibody (such as ipilimumab and tremelimumab); and an anti-PD-L1 antibody (such as durvalumab, atezolizumab, and avelumab).

Another embodiment of the present invention includes an agent for treating or preventing a cancer, comprising a TLR7 agonist which is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl) glycine, or a pharmaceutically acceptable salt thereof, which is used with an immune checkpoint inhibitor. Therein, one embodiment of the combination of a TLR7 agonist and an immune checkpoint inhibitor includes a combination of a TLR7 agonist which is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof; and a medicament that can inhibit the function of a molecular which is selected from the group consisting of: (1) CTLA-4; (2) PD-1; (3) PD-L1; (4) PD-L2; (5) LAG-3; (6) KIR; (7) TIM-3; (8) B7-H3; (9) B7-H4; (10) VISTA; (11) HVEM; (12) BTLA; (13) CD160; (14) GAL9; (15) TIGIT; (16) PVR; (17) BTNL2; (18) BTN1A1; (19) BTN2A2; (20) BTN3A2; and (21) CSF1-R.

Another embodiment of the combination of a TLR7 agonist and an immune checkpoint inhibitor includes a combination of a TLR7 agonist which is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl) glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof; and a medicament that can inhibit the function of a molecular which is selected from the group consisting of: CTLA-4; PD-1; PD-L1; LAG-3; TIM-3; VISTA; HVEM; BTLA; CD160; TIGIT; and PVR.

Another embodiment of the combination of a TLR7 agonist and an immune checkpoint inhibitor includes a combination of a TLR7 agonist which is selected from the group consisting of: N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, and a pharmaceutically acceptable salt thereof; and an antibody which is selected from the group consisting of: an anti-CTLA-4 antibody (such as ipilimumab, tremelimumab, BMS-986218, MK-1308, ADU-1604, BMS-986249, CS-1002, BCD-145, and REGN-4659); an anti-PD-1 antibody (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100); an anti-PD-L1 antibody (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and BMS-936559); an anti-LAG-3 antibody (such as IMP-321 and BMS-986016); an anti-TIM-3 antibody; anti-VISTA antibody; an anti-HVEM antibody; an anti-BTLA antibody; an anti-CD160 antibody; an anti-TIGIT antibody; and an anti-PVR antibody.

Another embodiment of the combination of a TLR7 agonist and an immune checkpoint inhibitor includes a combination of a TLR7 agonist which is selected from the group consisting of: N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, and a pharmaceutically acceptable salt thereof; and an antibody which is selected from the group consisting of: an anti-CTLA-4 antibody (such as ipilimumab, tremelimumab, BMS-986218, MK-1308, ADU-1604, BMS-986249, CS-1002, BCD-145, and REGN-4659); an anti-PD-1 antibody (such as nivolumab, pembrolizumab, cemiplimab, tislelizumab, dostarlimab, spartalizumab, camrelizumab, genolimzumab, sintilimab, JNJ-3283, BI-754091, INCMGA-00012, ABBV-181, CC-90006, AGEN-2034w, GSL-010, LZM-009, Sym-021, AB-122, AK-105, CS-1003, HLX-10, and BCD-100); and an anti-PD-L1 antibody (such as durvalumab, atezolizumab, avelumab, STI-1014, CK-301, BMS-986189, LY-3300054, CX-072, CBT-502, FAZ-053, FS-118, HTI-1088, MSB-2311, BGB-A333, IMC-001, HLX-20, A-167, and EMS-936559).

Another embodiment of the combination of a TLR7 agonist and an immune checkpoint inhibitor includes a combination of a TLR7 agonist which is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl) glycine, or a pharmaceutically acceptable salt thereof; and an anti-PD-1 antibody (nivolumab, pembrolizumab, cemiplimab, tislelizumab, dostarlimab, spartalizumab, camrelizumab, genolimzumab, sintilimab); an anti-PD-L1 antibody (durvalumab, atezolizumab, avelumab); or an anti-CTLA-4 antibody (ipilimumab, tremelimumab).

The "effector memory T cell" used herein means a cell population of CD8-positive T-cell, which is circulating within an organism for a long time, and when the cell finds an antigen expressed on a cell surface of a cancer cell, the cell can proliferate for a short period to kill the cancer cell. The agent for inducing effector memory T cell is a medicament which can sustain its anticancer activity for a long period through the induction of effector memory T cell, and can inhibit the exacerbation or relapse of cancer. Thus, the agent for inducing effector memory T cell in the present invention which comprises a combination of an immune checkpoint inhibitor and a TLR7 agonist can be used as a medicament for treating a cancer, preventing a cancer, or preventing relapse of a cancer.

The "MHC class I" used herein means a molecule which can combine with a peptide fragment of a cancer antigen expressed on a cancer cell to present the antigen peptide fragment extracellularly. The agent for inducing MHC class I is a medicament which can increase the amount of the antigen presentation on a cancer cell, and enhance the recognition ability of CTL for attacking a cancer to enhance the anticancer immunological effect. Thus, the agent for inducing MHC class I in the present invention which comprises a combination of an immune checkpoint inhibitor and a TLR7 agonist can be used as a medicament for treating or preventing a cancer, which exhibits more potent anticancer effect than each single administration.

The "cancer" used herein means a broad concept including solid cancers and blood cancers.

The solid cancer includes non-small-cell lung cancer, small cell lung cancer, pancreatic cancer, malignant melanoma, renal cell carcinoma, gastric cancer, colon cancer, rectal cancer, small intestinal cancer, breast cancer, germ cell cancer, bladder cancer, prostate cancer, endometrial cancer, cervical cancer, ovarian cancer, liver cancer, Merkel cell carcinoma, bone cancer, head and neck cancer, cutaneous or intraorbital malignant melanoma, anal cancer, testicular cancer, esophageal cancer, endocrine system cancer, thyroid cancer, parathyroid cancer, adrenal cancer, soft tissue sarcoma, urothelial cancer, penile cancer, glioblastoma multiforme, and brain tumor.

The blood cancer includes chronic or acute leukemia including acute myeloid leukemia, chronic myeloid leukemia, acute lymphoblastic leukemia, and chronic lymphocytic leukemia; myelodysplastic syndrome; multiple myeloma; malignant lymphoma including Hodgkin's lymphoma and non-Hodgkin's lymphoma.

The "cancer cell" used herein means individual cells composing a solid cancer or a blood cancer, which proliferate unlimitedly.

The "relapse with a cancer" or "relapse of a cancer" means that, in treating a solid cancer, the growth inhibition/reduction of the tumor goes well for a certain period through surgery or already-existing therapeutic approach, but then the tumor is again developed at the initial site or at a distal site. In treating a blood cancer, it means that, the hematological remission (which is a state keeping a certain level or less of cancer cells in blood), or the cytogenetic remission (which is a state wherein cancer-related genes are not detected in blood) goes well for a certain period through already-existing therapeutic approach, but then cancer cells arise in blood again.

The "having refractoriness to immune checkpoint inhibitors" for a solid cancer means a state wherein tumor enlargement cannot be suppressed even by administering an immune checkpoint inhibitor. The "having refractoriness to anti-PD-1 antibody" means a state wherein tumor enlargement cannot be suppressed even by administering the above-mentioned anti-PD-1 antibody. The "having refractoriness to anti-PD-L1 antibody" means a state wherein tumor enlargement cannot be suppressed even by administering the above-mentioned anti-PD-L1 antibody.

For a blood cancer, the "having refractoriness to immune checkpoint inhibitors" means a state wherein the increase in the number of cancer cells in blood cannot be suppressed even by administering an immune checkpoint inhibitor. The "having refractoriness to anti-PD-1 antibody" means a state wherein the increase in the number of cancer cells in blood cannot be suppressed even by administering the above-mentioned anti-PD-1 antibody. The "having refractoriness to anti-PD-L1 antibody" means a state wherein the increase in the number of cancer cells in blood cannot be suppressed even by administering the above-mentioned anti-PD-L1 antibody.

The "having a long-term anticancer immunity" means that an immune cell recognizing a cancer cell-specific antigen lives for a long term and thereby the anticancer effect persists for a long term. It is well known that, even if the treatment of a cancer is in a successful state temporarily, i.e., cancer cells regress or the number of cancer cells decrease, cancer cells increase again to lead to relapse of cancer as the number of immune cells which can recognize cancer cells in body and attack them decreases over time. If immune cells memorizing a cancer-specific antigen live for a long term, however, it is possible to lower the possibility of cancer relapse after successful treatment of cancer.

The drug of the present invention exhibits potent anticancer effect by using a TLR7 agonist and an immune checkpoint inhibitor in combination. By further using some other drug(s) or therapy method(s) in multiple combinations (for example, multidrug therapy), the effect can be more enhanced and the QOL of patients can be improved. The drug or therapy method to be further used in multiple combinations includes, for example, a chemotherapeutic agent (such as Ifosfamide, cyclophosphamide, dacarbazine, temozolomide, nimustine, busulfan, melphalan, enocitabine, capecitabine, carmofur, gemcitabine, cytarabine, tegafur, nelarabine, fluorouracil, fludarabine, pemetrexed, pentostatin, methotrexate, irinotecan, etoposide, sobuzoxane, docetaxel, paclitaxel, vinorelbine, vincristine, vindesine, vinblastine, actinomycin D, aclarubicin, idarubicin, epirubicin, daunorubicin, doxorubicin, pirarubicin, bleomycin, peplomycin, mitomycin C, mitoxantrone, oxaliplatin, carboplatin, cisplatin, and nedaplatin), a kinase inhibitor (such as gefitinib, erlotinib, osimertinib, afatinib, imatinib, dasatinib, bosutinib, vandetanib, sunitinib, axitinib, pazopanib, lenvatinib, lapatinib, nintedanib, nilotinib, ibrutinib, crizotinib, ceritinib, alectinib, tofacitinib, baricitinib, ruxolitinib, olaparib, sorafenib, vemurafenib, dabrafenib, trametinib, and palbociclib), a monoclonal antibody (such as rituximab, cetuximab, trastuzumab, bevacizumab, mogamulizumab, pertuzumab, alemtuzumab, panitumumab, ofatumumab, ramucirumab, and denosumab), an immunostimulant (such as TLR3 agonist, TLR4 agonist, TLR8 agonist, TLR9 agonist, STING agonist, and NOD2 agonist), a cancer vaccine (MHC class I-cancer antigen peptide derived from a cancer antigen protein selected from the group consisting of WT1, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a, MART-1/Melan-A, MC1R, Gp100, PSA, PSM, Tyrosinase, Proteinase 3, TRP-1, TRP-2, ART-4, CAMEL, CEA, Ep-CAM, Cyp-B, Her2/neu, VEGFR, hTERT, hTRT, iCE, MUC1, MUC2, PRAME, P15, RU1, RU2, SART-1, SART-2, SART-3, AFP, β-Catenin, Caspase-8, CDK-4, ELF2, GnT-V, G250, HSP70-2M, HST-2, KIAA0205, MUM-1, MUM-2, MUM-3, Myosin, RAGE, SART-2, TRP-2, 707-AP, Survivin, Livin, and SYT-SSX), and radiotherapy. The present invention may be used along with one or more drugs or therapy methods mentioned above. Preferably it includes radiotherapy.

The drug of the present invention may be used as solid or liquid medicine for oral administration, or injection, topical agent, suppository, inhalant, or nasal absorption agent for parenteral administration. The solid medicine for oral administration includes a tablet, a pill, a capsule, a powder, and a granule. The capsule includes hard and soft capsules. And, the tablet includes a sublingual tablet, an oral paste tablet, and an oral rapidly-disintegrating tablet.

As for the above solid medicine for oral administration, one or more active ingredients may be directly administered, or may be mixed with an excipient (such as lactose, mannitol, glucose, microcrystalline cellulose, and starch), a binder (such as hydroxypropylcellulose, polyvinylpyrrolidone, and magnesium aluminometasilicate), a disintegrant (such as calcium cellulose glycolate), a lubricant (such as magnesium stearate), a stabilizing agent, a solubilizing adjuvant (such as glutamate and aspartate), etc. to be formulated in conventional means, and the formulation may be administered. And, if necessary, the formulation may be coated with a coating agent (such as white soft sugar, gelatin, hydroxypropylcellulose, and hydroxypropylmethylcellulose phthalate), or with two or more coating layers. In addition, the above solid medicine for oral administration also includes capsule formulation composed of absorbable material such as gelatin. And, as appropriate, a conventional antiseptic agent, antioxidant, colorant, sweetening agent, etc. may be added thereto.

The above oral rapidly-disintegrating tablet can be prepared in a known manner. For example, one or more active ingredients may be directly administered, or bulk powder thereof or granulated particle of the bulk powder may be coated with a coating agent and a plasticizer, mixed with an excipient, a binder, a disintegrant, a lubricant, a dispersing agent, a stabilizing agent, a solubilizing adjuvant, a flavor, etc. to be formulated in conventional means, and the formulation may be administered. And, if necessary, the formulation may be coated with a coating agent, or with two or more coating layers. And, as appropriate, a conventional antiseptic agent, antioxidant, colorant, sweetening agent, etc. may be added thereto.

The above liquid medicine for oral administration may include a pharmaceutically acceptable water liquid, suspension, emulsion, syrup, elixir, etc. In order to prepare these liquid preparations, one or more active ingredients are dissolved, suspended, or emulsified in a conventional diluent such as purified water, ethanol, and a mixture thereof. In addition, these liquid preparations may comprise a humectant, a suspending agent, an emulsifying agent, a sweetening agent, a flavor, a fragrance, a preservative, a buffer, etc.

The above injection for parenteral administration may include a solution, a suspension, an emulsion, and a solid for injection which can be dissolved or suspended before using. The above injection to be used is prepared by dissolving, suspending, or emulsifying one or more active ingredients in a solvent. The solvent used herein includes, for example, distilled water for injection, saline, vegetable oil, an alcohols (such as propylene glycol, polyethylene glycol, and ethanol), and a mixture thereof. In addition, the injection used herein may comprise a stabilizing agent, a solubilizing adjuvant (e.g. amino acid such as glycine, glutamate, aspartate, Polysorbate™ 80, etc.), a pH adjuster to be generally used in pharmaceutical formulation (e.g. hydrochloric acid, sulfuric acid, nitric acid, acetic acid, citric acid, tartaric acid, lactic acid, maleic acid, phosphoric acid, sodium hydroxide, potassium hydroxide, aqueous ammonia, sodium acetate hydrate, anhydrous sodium acetate, sodium citrate hydrate, sodium dihydrogen citrate, sodium tartrate, disodium phosphate, dipotassium phosphate, sodium dihydrogenphosphate, potassium dihydrogenphosphate, trisodium phosphate, etc.), a suspending agent, an emulsifying agent, a dispersant, a soothing agent, a buffer, a preservative, a colorant, etc. These formulations are sterilized in final process or prepared in aseptic procedure. In addition, a sterile solid formulation such as a lyophilized formulation is prepared, and it may be used after it is dissolved in sterile/sterilized distilled water for injection or other solvents before using.

The other composition for parenteral administration includes suppository for rectal administration and pessary for vaginal administration, which comprises one or more active ingredients and is administered in conventional manner.

In one embodiment, the pharmaceutical composition comprising a TLR7 agonist may comprise one or more pharmaceutically acceptable carriers selected from the group consisting of trehalose, mannitol, glycine, methionine, citric acid, lactic acid, tartaric acid, acetic acid, trifluoroacetic acid, and a pH adjuster.

In one embodiment, the pharmaceutical composition comprising an immune checkpoint inhibitor may comprise one or more pharmaceutically acceptable carriers selected from the group consisting of mannitol, sodium citrate hydrate, sodium chloride, diethylenetriamine pentaacetic acid, Polysorbate™ 80, and a pH adjuster.

The administration method of a TLR7 agonist or an immune checkpoint inhibitor may be suitably chosen depending on each condition such as disease type, patient condition, and targeting site. The above administration method includes, for example, intravenous, intramuscular, intradermal, intraperitoneal, subcutaneous, or spinal administration by injection or infusion, or other parenteral administration routes. And, the "parenteral administration" used herein means an administration manner of normal injection except for enteral or topical administration, which includes intravenous, intramuscular, intraarterial, intrathecal, subcapsular, intraorbital, intracardiac, intradermal, intraperitoneal, transtracheal, subcutaneous, subepidermal, intraarticular, subcapsular, subarachnoid, intraspinal, epidural, and sternal injection or infusion, but should not limited thereto.

A TLR7 agonist in the present invention can effectively prevent or treat a cancer in combination with non-drug therapy as well as an immune checkpoint inhibitor. The non-drug therapy includes, for example, surgery, radiation therapy, gene therapy, thermotherapy, cryosurgery, and laser ablation, and two or more of these therapies may be combined. The timing of using such non-drug therapy is not limited, but, for example, the present drug or an immune checkpoint inhibitor to be administered with the present drug may be administered before or after using non-drug therapy such as surgery, or before or after using a combination of two or three non-drug therapies. These combinations can potentiate the effect of non-drug therapy such as inhibition of tolerance development, prolongation of disease-free survival, inhibition of cancer metastasis or relapse, and survival benefit.

The doses of a TLR7 agonist and an immune checkpoint inhibitor, the dosage form thereof, the frequency of administration, the term of one administration, etc. may be suitably chosen depending on each condition such as disease type, patient condition, and targeting site. The dose of a TLR7 agonist for one time is generally 0.0001 mg-1000 mg, preferably 0.001 mg-1000 mg, preferably 0.01 mg-100 mg, more preferably 0.1 mg-10 mg. The dose of an immune checkpoint inhibitor per kilogram of body weight is generally 0.0001 mg 1000 mg, preferably 0.001 mg-1000 mg, preferably 0.01 mg-100 mg, more preferably 0.1 mg-10 mg. The daily administration frequency of a TLR7 agonist is not limited, but it includes about 1 to 4 times a day, preferably about 1 to 3 times a day. The daily administration frequency of a TLR7 agonist is preferably once.

The administration schedule of the combination of a TLR7 agonist and an immune checkpoint inhibitor includes, administering a TLR7 agonist to a patient in a dose of 0.001 mg-1000 mg/subject once a week, totally 4-6 times; and 2-3 weeks later, administering once the same dosage as the above; then 3-4 weeks later, administering once the same dosage as the above; during the administration period of the TLR7 agonist, administrating an immune checkpoint inhibitor to the patient in a dose of 0.01 mg-1000 mg/subject once in two or three weeks. In the administration schedule, one single dose of a TLR7 agonist includes, preferably, 0.001-0.01 mg/subject, 0.01-0.1 mg/subject, 0.1 mg-1 mg/subject, 1 mg-3 mg/subject, 3 mg-10 mg/subject, 10-30 mg/subject, 30-100 mg/subject, 100-300 mg/subject, and 300-1000 mg/subject. And, one single dose of an immune checkpoint inhibitor includes, preferably, 0.01-0.1 mg/subject, 0.1-1 mg/subject, 1 mg-10 mg/subject, 10-100 mg/subject, 100-400 mg/subject, and 400 mg-1000 mg/subject, for each dose of a TLR7 agonist. In the combination therapy, the weight ratio of one single dose of a TLR7 agonist per that of an immune checkpoint inhibitor or a combined drug includes, for example, 0.1-1000, preferably 0.1-100, 0.1-10, 0.1-1, 1-1000, 10-1000, 100-1000, 1-100, 1-10, and 10-100.

The "therapeutically effective amount" used herein means the amount of a TLR7 agonist or an immune checkpoint inhibitor, or the amount of a combination of two or more of a TLR7 agonist and an immune checkpoint inhibitor, which can inhibit cancer progress completely or partially, or relieve one or more conditions of a cancer at least partially. The effective amount may be a therapeutically or prophylactically effective amount. The effective amount should be determined based on age and gender of patients, condition to be treated, severity of condition, desired outcome, etc. The effective amount for a certain patient may be determined based on a method known by a skilled person.

In the present invention, it is also expected that the CTL activity induced by a TLR7 agonist can be more activated with a combination of an immune checkpoint inhibitor to potentiate the tumor response in a host. Here, the cancers as the target in the present invention include solid cancers or blood cancers exemplified below.

The solid cancer herein includes non-small-cell lung cancer; small cell lung cancer; pancreatic cancer; malignant melanoma; renal cell carcinoma; gastric cancer; colon cancer; rectal cancer; small intestinal cancer; breast cancer; germ cell cancer; bladder cancer; prostate cancer; endometrial cancer; cervical cancer; ovarian cancer; liver cancer; Merkel cell carcinoma; bone cancer; head and neck cancer; cutaneous or intraorbital malignant melanoma; anal cancer; testicular cancer; esophageal cancer; endocrine system cancer; thyroid cancer; parathyroid cancer; adrenal cancer; soft tissue sarcoma; urothelial cancer; penile cancer; glioblastoma multiforme; and brain tumor.

The blood cancer herein includes chronic or acute leukemia including acute myeloid leukemia, chronic myeloid leukemia, acute lymphoblastic leukemia, and chronic lymphocytic leukemia; malignant lymphoma including Hodgkin's lymphoma and non-Hodgkin's lymphoma; myelodysplastic syndrome; and multiple myeloma.

An embodiment of cancers in the present invention includes, preferably, head and neck cancer, melanoma, kidney cancer, Hodgkin's disease, urothelial cancer, liver cancer, non-small-cell lung cancer, small cell cancer, gastric cancer, and Merkel cell carcinoma.

An embodiment of cancers in the present invention includes, more preferably, head and neck cancer, renal cell carcinoma, Hodgkin's lymphoma, non-small-cell lung cancer, and gastric cancer.

In addition, the induction of effector memory T cell or the induction of MHC class I can promote the immune response to a pathogen such as bacteria, fungi, and virus, as well as a cancer. Thus, with regard to an inducer of effector memory T cell for treating an infection such as HCV, HBV, and HIV, or an inducer of MHC class I for treating an infection such as HCV, HBV, and HIV, which comprises a TLR7 agonist with a combination of an immune checkpoint inhibitor, the both may be within the present invention.

The "mammal" used herein includes human and non-human animal. The non-human animal includes, for example, non-human primate, sheep, dogs, cats, horses, and cattle, but should not be limited thereto. The mammal used herein is preferably human, especially, a human patient who needs enhancement of immune response. Thus, the present invention is especially suitable for treating a human patient suffering from a disease which is expected to be cured by promoting T cell-mediated immune response.

In the present invention, a TLR7 agonist and an immune checkpoint inhibitor may be contained in separate dosage forms or in one single dosage form. That is, the drug of the present invention may be a drug comprising a TLR7 agonist for using along with an immune checkpoint inhibitor, a drug comprising an immune checkpoint inhibitor for using along with a TLR7 agonist, or a drug comprising a TLR7 agonist and an immune checkpoint inhibitor (i.e., a combination drug). The present invention may be provided as a kit, for example, such a kit may comprise a drug comprising a TLR7 agonist and a drug comprising an immune checkpoint inhibitor. The drug and kit of the present invention may be provided along with a package insert, a packaging container, a user instruction, etc. which describes dosage and administration about the combined use of a TLR7 agonist and an immune checkpoint inhibitor. In an embodiment of the present invention, the drug and kit of the present invention may be provided as a pharmaceutical for treating a cancer.

In the present invention, a TLR7 agonist and an immune checkpoint inhibitor may be administered simultaneously or separately. Furthermore, a TLR7 agonist and an immune checkpoint inhibitor may be administered simultaneously or separately with an additional combined drug. The "simultaneously administered" used herein means an administration in a common administration schedule, in which the active ingredients may be contained in a single dosage form or a separate dosage forms. When each ingredient is contained in separate dosage forms, all the dosage forms should be administered in single application. The "separately administered" used herein means "administered" in different administration schedules, i.e., one drug is administered, and then the other drug is administered at some interval, but either drug may be administered in first, and the interval is unlimited. The frequency of administration of each active ingredient may be identical or different, for example, one drug may be administered one a day, and the other drug may be administered two or more times a day.

In case that the active ingredients are contained in a single dosage form, the combination ratio may be suitably chosen depending on patient for administration, administration route, target disease, symptom, or a combination thereof. In case that the patient for administration is for example, a human, an immune checkpoint inhibitor or a combined drug may be used in an amount of 0.1-1000 parts by weight, preferably 0.1-100 parts by weight, 0.1-10 parts by weight, 0.1-1 parts by weight, 1-1000 parts by weight, 10-1000 parts by weight, 100-1000 parts by weight, 1-100 parts by weight, 1-10 parts by weight, or 10-100 parts by weight, per one part by weight of TLR7 agonist.

The pharmaceutical composition of the present invention may be used further in combination with another drug such as an antiemetic drug, a sleep-inducing drug, and an anti-seizure drug to suppress side effects.

A TLR7 agonist is a drug for activating cancer-reactive CTL in tumor, thus the dose of an immune checkpoint inhibitor might be reduced with a combination of a TLR7 agonist. That means that the combination has a possibility to reduce adverse event. Thus, the combination use of a TLR7 agonist and an immune checkpoint inhibitor might provide patients with a therapy which has both of higher efficacy and higher safety.

EXAMPLES

The present invention is explained in more detail in the following by referring to Examples, however, the present invention should not be limited thereto.

Example 1: Antitumor Activity of Combination Use of Anti-PD-1 Antibody and TLR7 Agonist $1 \times 10^6$ Cells of murine colon cancer cell line CT26 (ATCC) were transplanted to the ventral flank of 48 female 6-week-old Balb/c mice. Five days later, the mice were divided into four groups. In vehicle administration group, saline was intravenously administered once a week, and 200 μg of Rat IgG2a isotype control antibody (Bioxcell) was intraperitoneally administered twice a week. In TLR7 agonist administration group, a TLR7 agonist, N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine (hereinafter, referred to as "Compound 1") was administered into a vein in a dose of 5 mg/kg once a week, and 200 μg of Rat IgG2a isotype control antibody (Bioxcell) was intraperitoneally administered twice a week. In anti-PD-1 antibody administration group, 200 μg of anti-PD-1 antibody (Bioxcell) was intraperitoneally administered twice a week. In combination group of Compound 1 and anti-PD-1 antibody, Compound 1 was intravenously administered in a dose of 5 mg/kg once a week, and 200 μg of anti-PD-1 antibody (Bioxcell) was intraperitoneally administered twice a week. After the transplantation of the tumor cell, the tumor volume was measured twice a week, and the body weight was checked once a week until the 23rd day. The tumor volume was obtained by measuring long axis and short axis of the tumor and calculating by a math formula of (short axis)×(short axis)×(long axis)×0.5.

The result is shown in FIG. 1. The figure shows tumor growth curves of each administration group. The ordinate denotes tumor volume, and the abscissa denotes elapsed days from the transplantation of the tumor cell.

The results showed that the tumor-volume variation in the anti-PD-1 antibody (single drug) administration group was not so different from that of the vehicle administration group, while a tumor growth inhibition was observed in the Compound 1 (single drug) administration group and the combination group of Compound 1 and anti-PD-1 antibody. In addition, the combination group of Compound 1 and anti-PD-1 antibody showed a significant tumor growth inhibition compared with the Compound 1 (single drug) administration group. Thus, it is thought that the antitumor activity can be synergistically enhanced by combining an anti-PD-1 antibody and Compound 1.

Example 2: Effect of Tumor-Infiltrating Lymphocyte (TIL) for Increasing Effector Memory T Cell $1 \times 10^6$ Cells of murine colon cancer cell line CT26 (ATCC) were transplanted to the ventral flank of 48 female 6-week-old Balb/c mice. Five days later, the mice were divided into four groups. In vehicle administration group, saline was intravenously administered once a week, and 200 μg of Rat IgG2a isotype control antibody (Bioxcell) was intraperitoneally administered twice a week. In Compound 1 administration group, Compound 1 was intravenously administered in a dose of 5 mg/kg once a week, and 200 μg of Rat IgG2a isotype control antibody (Bioxcell) was intraperitoneally administered twice a week. In anti-PD-1 antibody administration group, 200 μg of anti-PD-1 antibody (Bioxcell) was intraperitoneally administered twice a week. In combination group of Compound 1 and anti-PD-1 antibody, Compound 1 was intravenously administered in a dose of 5 mg/kg once a week, and 200 μg of anti-PD-1 antibody (Bioxcell) was intraperitoneally administered twice a week. After the transplantation of the tumor cell, the tumor was picked out on the 23rd day, and a cell suspension of the tumor was prepared by using a tumor dissociation kit (Miltenyi) and a gentle macs dissociates (Miltenyi). The cell suspension was density-gradient-centrifuged with Percoll to give a cell suspension in which lymphocyte was concentrated. Further, the cell suspension was treated with ACK buffer to hemolyze erythrocyte. The obtained cell suspension was stained with fluoresceinated anti-CD8, anti-CD62L, and anti-CD127 antibodies, and analyzed by flow cytometry (FACS) method. The cell population containing CD8-positive cell, CD62L-negative cell, and CD127-positive cell, each of which is a cell surface antigen of effector memory T cell, was used as effector memory T cell.

Figure 2:
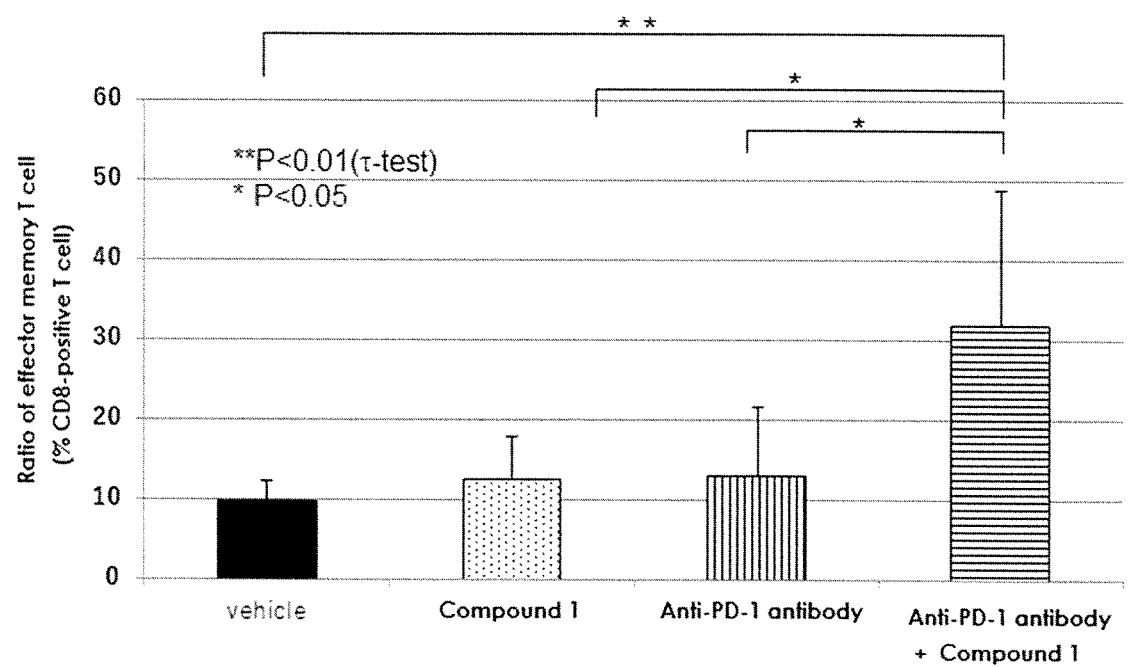
FIG. 2 shows each ratio of the effector memory T cell in CD8-positive cell, in each administration group, which was obtained by FACS analysis.

The result is shown in FIG. 2. The figure shows each ratio of the effector memory T cell in CD8-positive cell of each administration group, which was obtained by FACS analysis. The result showed that the ratio of effector memory T cell in CD8-positive cell significantly increased in the combination group of Compound 1 and anti-PD-1 antibody.

In either single drug administration group of Compound 1 or an anti-PD-1 antibody, the ratio of effector memory T cell did not increase compared with the vehicle administration group, while the ratio of effector memory T cell significantly increased in the combination group of Compound 1 and anti-PD-1 antibody. Thus, it has been found that a long-term antitumor immune activity can be potentiated by combining Compound 1 and an anti-PD-1 antibody.

Example 3: Effect for Increasing MHC Class I (H-2Kd) on a Tumor $1\times10^6$ Cells of murine colon cancer cell line CT26 (ATCC) were transplanted to the ventral flank of 48 female 6-week-old Balb/c mice. Five days later, the mice were divided into four groups. In vehicle administration group, saline was intravenously administered once a week, and 200 μg of Rat IgG2a isotype control antibody (Bioxcell) was intraperitoneally administered twice a week. In Compound 1 administration group, Compound 1 was intravenously administered in a dose of 5 mg/kg once a week, and 200 μg of Rat IgG2a isotype control antibody (Bioxcell) was intraperitoneally administered twice a week. In anti-PD-1 antibody administration group, 200 μg of anti-PD-1 antibody (Bioxcell) was intraperitoneally administered twice a week. In combination group of Compound 1 and anti-PD-1 antibody, Compound 1 was intravenously administered in a dose of 5 mg/kg once a week, and 200 μg of anti-PD-1 antibody (Bioxcell) was intraperitoneally administered twice a week. After the transplantation of the tumor cell, the tumor was picked out on the 23rd day, and a cell suspension of the tumor was prepared by using a tumor dissociation kit (Miltenyi) and a gentle macs dissociater (Miltenyi). The cell suspension was stained with fluoresceinated anti-CD45 antibody and anti-H-2Kd antibody, and H-2Kd on the cancer cell was detected as CD45-negative and H-2Kd-positive fractions by flow cytometry method.

Figures 3, 4:
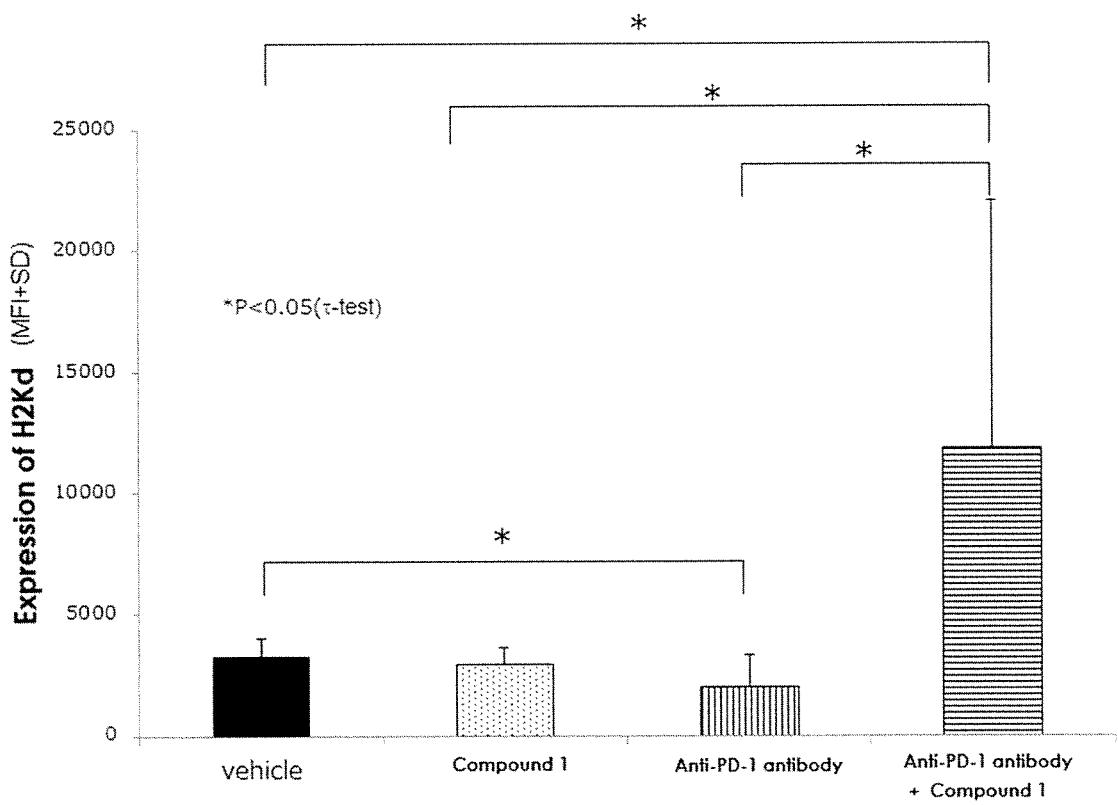
FIG. 3 shows each MFI of H-2Kd in each administration group, which was obtained by FACS analysis.
FIG. 4 shows the number of therapeutically-responsible subjects in each administration group and the number of engraftment-acceptable subjects after the re-transplantation.

The result is shown in FIG. 3. The figure shows each MFI of H-2Kd in each administration group, which was obtained by FACS analysis. The result showed that the mean fluorescent intensity (MFI) of H-2Kd in the combination group of Compound 1 and anti-PD-1 antibody was significantly higher than any other groups.

In either single drug administration group of Compound 1 or an anti-PD-1 antibody, the mean fluorescent intensity of H-2Kd was not so different from that of the vehicle administration group, while the mean fluorescent intensity of H-2Kd in the combination group of Compound 1 and anti-PD-1 antibody was significantly higher than any other groups. Thus, it is thought that the antitumor activity can be synergistically enhanced by combining Compound 1 and an anti-PD-1 antibody.

Example 4: Memory Effect to Reject Engraftment after Re-Transplantation $1\times10^6$ Cells of murine colon cancer cell line CT26 (ATCC) were transplanted to the ventral flank of 48 female 6-week-old Balb/c mice. Five days later, the mice were divided into four groups. In vehicle administration group, saline was intravenously administered once a week, and 200 μg of Rat IgG2a isotype control antibody (Bioxcell) was intraperitoneally administered twice a week. In Compound 1 administration group, Compound 1 was intravenously administered in a dose of 5 mg/kg once a week, and 200 μg of Rat IgG2a isotype control antibody (Bioxcell) was intraperitoneally administered twice a week. In anti-PD-1 antibody administration group, 200 μg of anti-PD-1 antibody (Bioxcell) was intraperitoneally administered twice a week. In combination group of Compound 1 and anti-PD-1 antibody, Compound 1 was intravenously administered in a dose of 5 mg/kg once a week, and 200 μg of anti-PD-1 antibody (Bioxcell) was intraperitoneally administered twice a week. After the transplantation of the tumor cell, the mice whose tumor volume was not more than 500 mm$^3$ on 23rd day were separated as therapeutically-responsible subjects, the tumor thereof was excised, and then the mice were bred for another weeks. When $1\times10^6$ cells of the CT26 cell were re-transplanted to the alive mice, 6 mice among 6 subject mice in combination group of Compound 1 and anti-PD-1 antibody did not accept the engraftment.

The result is shown in FIG. 4. The figure shows the number of cured mice in each administration group and the number of mice with tumor growth after the re-transplantation. The result showed that tumor growth after the re-transplantation was not observed in the combination of Compound 1 and the anti-PD-1 antibody. Thus, the combination is expected to have a long-term antitumor activity and to prevent recurrence.

Example 5: Antitumor Activity of Combination Use of Anti-CTLA-4 Antibody and TLR7 Agonist $1\times10^6$ Cells of murine colon cancer cell line CT26 (ATCC) were transplanted to the ventral flank of 40 female 7-week-old Balb/c mice. Seven days later, the mice were divided into four groups. In vehicle administration group, saline was intravenously administered once a week, and 200 μg of Rat IgG2a isotype control antibody (Bioxcell) was intraperitoneally administered twice a week. In TLR7 agonist administration group, Compound 1 was intravenously administered in a dose of 5 mg/kg once a week, and 200 μg of Rat IgG2a isotype control antibody (Bioxcell) was intraperitoneally administered twice a week. In anti-CTLA-antibody administration group, 200 μg of anti-CTLA-4 antibody (Bioxcell) was intraperitoneally administered twice a week. In combination group of Compound 1 and anti-CTLA-4 antibody, Compound 1 was intravenously administered in a dose of 5 mg/kg once a week, and 200 μg of anti-CTLA-4 antibody (Bioxcell) was intraperitoneally administered twice a week. After the transplantation of the tumor cell, the tumor volume was measured twice a week, and the body weight was checked once a week until the 23rd day. The tumor volume was obtained by measuring long axis and short axis of the tumor and calculating by a math formula of (short axis)×(short axis)×(long axis)×0.5.

Figure 5:
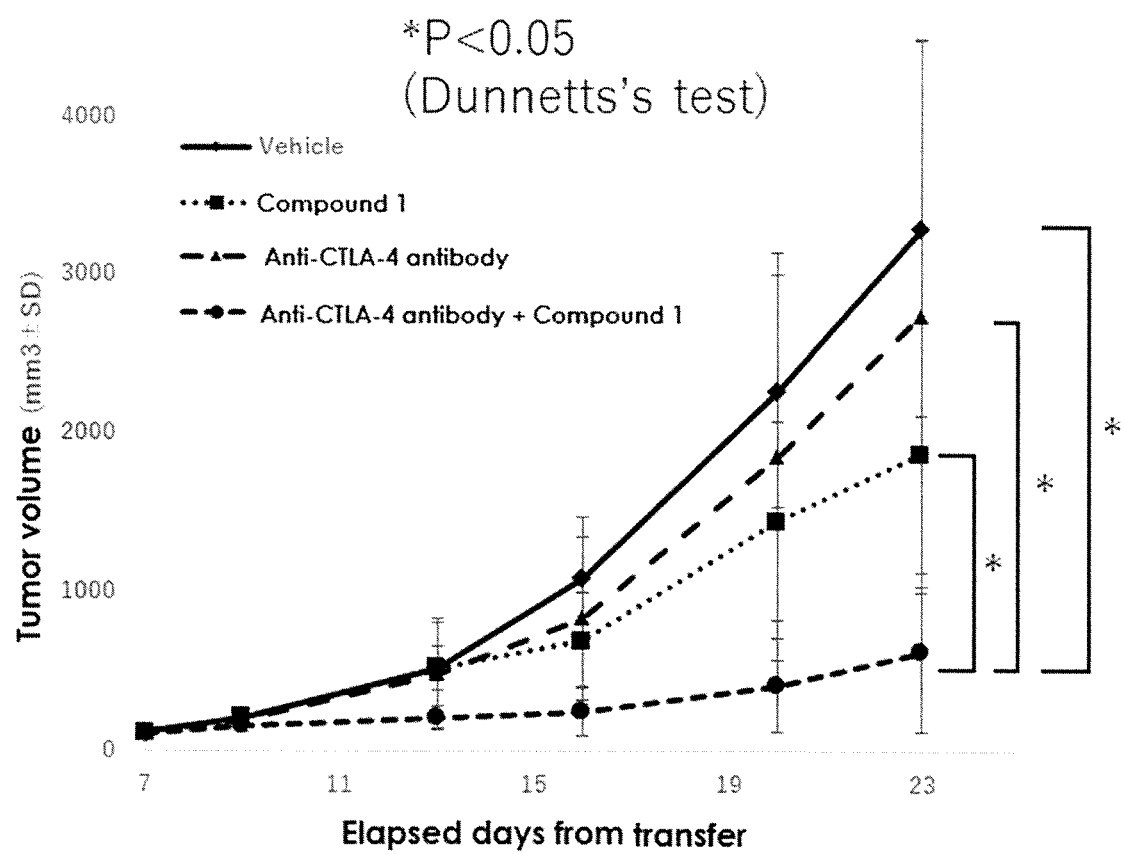
FIG. 5 shows tumor growth curves of each administration group. The ordinate denotes tumor volume, and the abscissa denotes elapsed days from the transplantation of the tumor cell.

The result is shown in FIG. 5. The figure shows tumor growth curves of each administration group. The ordinate denotes tumor volume, and the abscissa denotes elapsed days from the transplantation of the tumor cell.

The results showed that the tumor-volume variation in the anti-CTLA-4 antibody (single drug) administration group or the Compound 1 administration group was not so different from that of the vehicle administration group, while a significant tumor growth inhibition was observed in the combination group of Compound 1 and anti-CTLA-4 antibody. In addition, the combination group of Compound 1 and anti-CTLA-4 antibody showed a significant tumor growth inhibition compared with the Compound 1 administration group or the anti-CTLA-4 antibody administration group. Thus, it is thought that the antitumor activity can be synergistically enhanced by combining an anti-CTLA-4 antibody and Compound 1.

Example 6: Effect of Tumor-Infiltrating Lymphocyte (TIL) for Increasing Effector Memory T Cell $1\times10^6$ Cells of murine colon cancer cell line CT26 (ATCC) were transplanted to the ventral flank of 40 female 6-week-old Balb/c mice. Seven days later, the mice were divided into four groups. In vehicle administration group, saline was intravenously administered once a week, and 200 µg of Rat IgG2a isotype control antibody (Bioxcell) was intraperitoneally administered twice a week. In Compound 1 administration group, Compound 1 was intravenously administered in a dose of 5 mg/kg once a week, and 200 µg of Rat IgG2a isotype control antibody (Bioxcell) was intraperitoneally administered twice a week. In anti-CTLA-4 antibody administration group, 200 µg of anti-CTLA-4 antibody (Bioxcell) was intraperitoneally administered twice a week. In combination group of Compound 1 and anti-CTLA-4 antibody, Compound 1 was intravenously administered in a dose of 5 mg/kg once a week, and 200 µg of anti-CTLA-4 antibody (Bioxcell) was intraperitoneally administered twice a week. After the transplantation of the tumor cell, the tumor was picked out on the 26th day, and a cell suspension of the tumor was prepared by using a tumor dissociation kit (Miltenyi) and a gentle macs dissociater (Miltenyi). The cell suspension was density-gradient-centrifuged with Percoll to give a cell suspension in which lymphocyte was concentrated. Further, the cell suspension was treated with ACK buffer to hemolyze erythrocyte. The obtained cell suspension was stained with fluoresceinated anti-CD8, anti-CD62L, and anti-CD127 antibodies, and analyzed by flow cytometry (FACS) method. The cell population containing CD8-positive cell, CD62L-negative cell, and CD127-positive cell, each of which is a cell surface antigen of effector memory T cell, was used as effector memory T cell.

Figure 6:
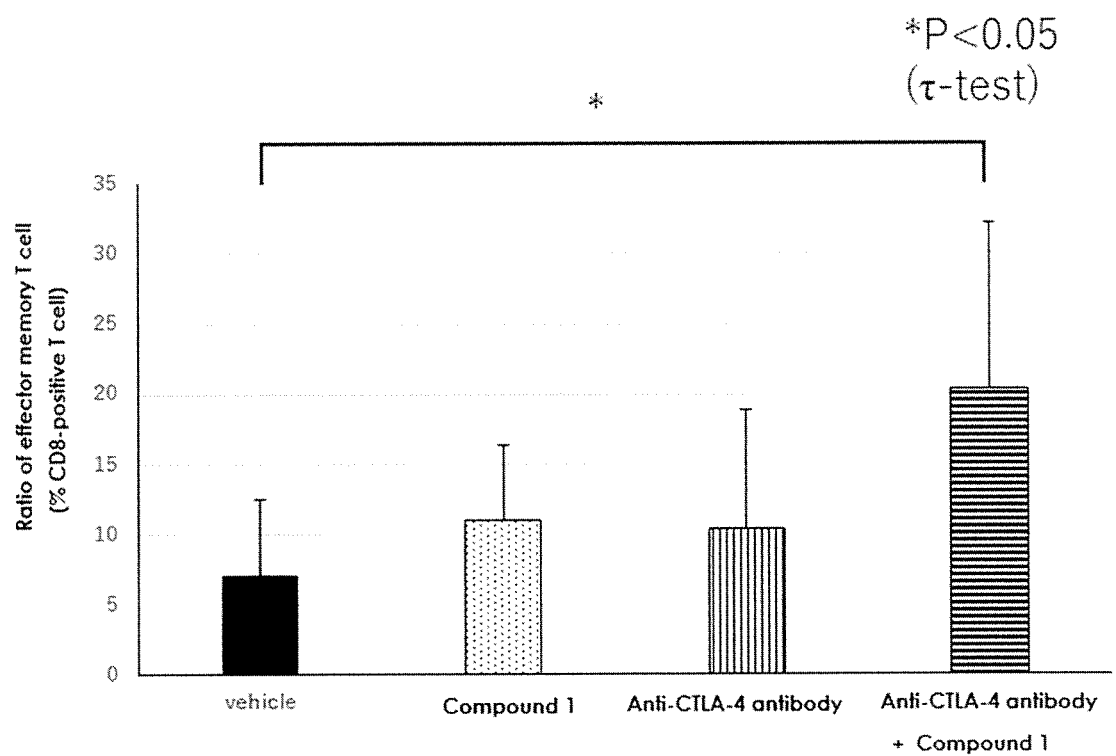
FIG. 6 shows each ratio of the effector memory T cell in CD8-positive cell, in each administration group, which was obtained by FACS analysis.

The result is shown in FIG. 6. The figure shows each ratio of the effector memory T cell in CD8-positive cell of each administration group, which was obtained by FACS analysis. The result showed that the ratio of effector memory T cell in CD8-positive cell significantly increased in the combination group of Compound 1 and anti-CTLA-4 antibody, compared with the vehicle administration group.

In either single drug administration group of Compound 1 or an anti-CTLA-4 antibody, the ratio of effector memory T cell did not increase compared with the vehicle administration group, while the ratio of effector memory T cell significantly increased in the combination group of Compound 1 and anti-CTLA-4 antibody. Thus, it has been found that a long-term antitumor immune activity can be potentiated by combining Compound 1 and an anti-CTLA-4 antibody.

Example 7: Effect on MHC Class I (H-2Kd) on Tumor $1 \times 10^6$ Cells of murine colon cancer cell line CT26 (ATCC) were transplanted to the ventral flank of 40 female 6-week-old Balb/c mice. Seven days later, the mice were divided into four groups. In vehicle administration group, saline was intravenously administered once a week, and 200 µg of Rat IgG2a isotype control antibody (Bioxcell) was intraperitoneally administered twice a week. In Compound 1 administration group, Compound 1 was intravenously administered in a dose of 5 mg/kg once a week, and 200 µg of Rat IgG2a isotype control antibody (Bioxcell) was intraperitoneally administered twice a week. In anti-CTLA-antibody administration group, 200 µg of anti-CTLA-4 antibody (Bioxcell) was intraperitoneally administered twice a week. In combination group of Compound 1 and anti-CTLA-4 antibody, Compound 1 was intravenously administered in a dose of 5 mg/kg once a week, and 200 µg of anti-CTLA-4 antibody (Bioxcell) was intraperitoneally administered twice a week. After the transplantation of the tumor cell, the tumor was picked out on the 26th day, and a cell suspension of the tumor was prepared by using a tumor dissociation kit (Miltenyi) and a gentle macs dissociater (Miltenyi). The cell suspension was stained with fluoresceinated anti-CD45 antibody and anti-H-2Kd antibody, and H-2Kd on the cancer cell was detected as CD45-negative and H-2Kd-positive fractions by flow cytometry method.

The result showed that there was not so significant difference among each group. However, the mean fluorescent intensity of H-2Kd in the combination group of Compound 1 and anti-CTLA-4 antibody tended to go up and Example 5 showed a synergistic antitumor activity, thus it is thought that the MHC class I (H-2Kd) in the tumor is enhanced in the combination group.

INDUSTRIAL APPLICABILITY

The present invention is utilizable in pharmaceutical field, for example, in development of a drug for treating and preventing a cancer, or in manufacture thereof.

The invention claimed is:

1. A method for inducing an effector memory T cell response or inducing an MHC class I response in a human patient in need thereof, comprising
   administering to the human patient a therapeutically effective amount of a TLR7 agonist in combination with a therapeutically effective amount of an immune checkpoint inhibitor,
   wherein the TLR7 agonist is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof, and
   the immune checkpoint inhibitor is an anti-PD-1 antibody, or an anti-CTLA-4 antibody, and
   wherein the TLR7 agonist is administered prior or posterior to the immune checkpoint inhibitor, and
   wherein the human patient has a cancer and is refractory to the immune checkpoint inhibitor.

2. The method according to claim 1, wherein the cancer is selected from the group consisting of non-small-cell lung cancer, small cell lung cancer, pancreatic cancer, malignant melanoma, renal cell carcinoma, gastric cancer, colon cancer, rectal cancer, small intestinal cancer, breast cancer, germ cell cancer, bladder cancer, prostate cancer, endometrial cancer, cervical cancer, ovarian cancer, liver cancer, Merkel cell carcinoma, bone cancer, head and neck cancer, cutaneous malignant melanoma, intraorbital malignant melanoma, anal cancer, testicular cancer, esophageal cancer, endocrine system cancer, thyroid cancer, parathyroid cancer, adrenal cancer, soft tissue sarcoma, urothelial cancer, penile cancer, glioblastoma multiforme, brain tumor, chronic leukemia, acute leukemia, malignant lymphoma, myelodysplastic syndrome, and multiple myeloma.

3. The method according to claim 2, wherein the cancer is acute myeloid leukemia, chronic myeloid leukemia, acute lymphoblastic leukemia, chronic lymphocytic leukemia, Hodgkin's lymphoma, or non-Hodgkin's lymphoma.

4. The method according to claim 1, wherein the human patient has relapsed with the cancer.

5. The method according to claim 1, which effects a long-term anticancer immunity.

6. The method according to claim 1, wherein the TLR7 agonist is N-{4-[(2-amino-4-{[(3S)-1-hydroxyhexan-3-yl]

amino}-6-methylpyrimidin-5-yl)methyl]-3-methoxybenzyl}-N-(2,2,2-trifluoroethyl)glycine, or a pharmaceutically acceptable salt thereof.

7. The method according to claim 1, wherein the immune checkpoint inhibitor is pembrolizumab.

8. The method according to claim 1, wherein the immune checkpoint inhibitor is an anti-PD-1 antibody.

9. The method according to claim 1, wherein the immune checkpoint inhibitor is an anti-CTLA-4 antibody.

10. The method according to claim 1, wherein the anti-PD-1 antibody is nivolumab, pembrolizumab, cemiplimab, tislelizumab, dostarlimab, spartalizumab, camrelizumab, sintilimab, BI-754091, ABBV-181, CC-90006, AGEN-2034w, LZM-009, Sym-021, HLX-10, or BCD-100,
the anti-CTLA-4 antibody is ipilimumab, tremelimumab, BMS-986218, MK-1308, or BMS-986249.

11. The method according to claim 1, wherein the TLR7 agonist and the immune checkpoint inhibitor are simultaneously administered.

12. The method according to claim 1, wherein the TLR7 agonist and the immune checkpoint inhibitor are separately administered.

13. The method according to claim 1, wherein the TLR7 agonist is administered prior to the immune checkpoint inhibitor.

14. The method according to claim 1, wherein the TLR7 agonist is administered posterior to the immune checkpoint inhibitor.

15. The method according to claim 1, wherein the method induces an effector memory T cell response in the human patient in need thereof.

16. The method according to claim 1, wherein the method induces an MHC class I response in the human patient in need thereof.

17. A method for treating a cancer in a human patient in need thereof, comprising
administering to the human patient a therapeutically effective amount of a TLR7 agonist selected from N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof,
in combination with a therapeutically effective amount of an immune checkpoint inhibitor, wherein the immune checkpoint inhibitor is an anti-PD-1 antibody or an anti-CTLA-4 antibody, and
wherein the human patient is refractory to the immune checkpoint inhibitor.

18. The method according to claim 17, wherein the TLR7 agonist is N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, or a pharmaceutically acceptable salt thereof.

19. The method according to claim 17, wherein the immune checkpoint inhibitor is pembrolizumab.

20. The method according to claim 17, wherein the immune checkpoint inhibitor is an anti-PD-1 antibody.

21. The method according to claim 17, wherein the immune checkpoint inhibitor is an anti-CTLA-4 antibody.

22. The method according to claim 17, wherein the anti-PD-1 antibody is nivolumab, pembrolizumab, cemiplimab, tislelizumab, dostarlimab, spartalizumab, camrelizumab, sintilimab, BI-754091, ABBV-181, CC-90006, AGEN-2034w, LZM-009, Sym-021, HLX-10, or BCD-100, the anti-CTLA-4 antibody is ipilimumab, tremelimumab, BMS-986218, MK-1308, or BMS-986249.

23. The method according to claim 17, wherein the human patient suffers from relapse of the cancer.

24. The method according to claim 17, wherein the method effects a long-term anticancer immunity.

25. A method for treating a cancer in a human patient in need thereof, which comprises administering to the human patient a therapeutically effective amount of N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof, and a therapeutically effective amount of an immune checkpoint inhibitor, wherein the immune checkpoint inhibitor is an anti-PD-1 antibody or an anti-CTLA-4 antibody, and
wherein the human patient is refractory to the immune checkpoint inhibitor.

26. The method according to claim 1, wherein the cancer is chosen from head and neck cancer, renal cell carcinoma, Hodgkin's lymphoma, non-small-cell lung cancer, and gastric cancer.

27. The method of according to claim 17, wherein the cancer is chosen from non-small-cell lung cancer; small cell lung cancer; pancreatic cancer; malignant melanoma; renal cell carcinoma; gastric cancer; colon cancer; rectal cancer; small intestinal cancer; breast cancer; germ cell cancer; bladder cancer; prostate cancer; endometrial cancer; cervical cancer; ovarian cancer; liver cancer; Merkel cell carcinoma; bone cancer; head and neck cancer; cutaneous or intraorbital malignant melanoma; anal cancer; testicular cancer; esophageal cancer; endocrine system cancer; thyroid cancer; parathyroid cancer; adrenal cancer; soft tissue sarcoma; urothelial cancer; penile cancer; glioblastoma multiforme; brain tumor; chronic or acute leukemia; malignant lymphoma; myelodysplastic syndrome; and multiple myeloma.

28. The method according to claim 27, wherein the chronic or acute leukemia is acute myeloid leukemia, chronic myeloid leukemia, acute lymphoblastic leukemia, or chronic lymphocytic leukemia, and wherein the malignant lymphoma is Hodgkin's lymphoma or non-Hodgkin's lymphoma.

29. The method according to claim 17, wherein the cancer is chosen from head and neck cancer, renal cell carcinoma, Hodgkin's lymphoma, non-small-cell lung cancer, and gastric cancer.

30. The method of according to claim 25, wherein the cancer is chosen from non-small-cell lung cancer; small cell lung cancer; pancreatic cancer; malignant melanoma; renal cell carcinoma; gastric cancer; colon cancer; rectal cancer; small intestinal cancer; breast cancer; germ cell cancer; bladder cancer; prostate cancer; endometrial cancer; cervical cancer; ovarian cancer; liver cancer; Merkel cell carcinoma; bone cancer; head and neck cancer; cutaneous or intraorbital malignant melanoma; anal cancer; testicular cancer; esophageal cancer; endocrine system cancer; thyroid cancer; parathyroid cancer; adrenal cancer; soft tissue sarcoma; urothelial cancer; penile cancer; glioblastoma multiforme; brain tumor; chronic or acute leukemia malignant lymphoma; myelodysplastic syndrome; and multiple myeloma.

31. The method according to claim 30, wherein the chronic or acute leukemia is acute myeloid leukemia, chronic myeloid leukemia, acute lymphoblastic leukemia, or chronic lymphocytic leukemia, and wherein the malignant lymphoma is Hodgkin's lymphoma or non-Hodgkin's lymphoma.

32. The method according to claim 25, wherein the cancer is chosen from head and neck cancer, renal cell carcinoma, Hodgkin's lymphoma, non-small-cell lung cancer, and gastric cancer.

33. A method for inducing an effector memory T cell response or inducing an MHC class I response in a human patient in need thereof, comprising:
 administering to the human patient a therapeutically effective amount of TLR7 agonist sufficient for TLR7 activation to produce cytokine induction and enhancement of antigen presentation in the mammal, wherein the TLR7 agonist is chosen from N-{4-[(2-amino-4-{[(3S)-1-hydroxyhexan-3-yl]amino}-6-methylpyrimidin-5-yl)methyl]-3-methoxybenzyl}-N-(2,2,2-trifluoroethyl)glycine, N-{4-[(2-amino-4-{[(3S)-1-hydroxyhexan-3-yl]amino}-6-methylpyrimidin-5-yl)methyl]-3-methoxybenzyl}-N-(2,2-difluoroethyl)glycine, or a pharmaceutically acceptable salt thereof; and
 administering to the human patient a therapeutically effective amount of an immune checkpoint inhibitor sufficient to inhibit immune checkpoint molecules that suppress the function of effector T cells in the human patient, wherein the immune checkpoint inhibitor is chosen from an anti-PD-1 antibody or an anti-CTLA-4 antibody;
wherein the TLR7 agonist and the checkpoint inhibitor are in a weight ratio effective to increase the amount of effector memory T cells or the amount of MHC class I molecules greater than the sum of any increase in amount of effector memory T cells or the amount of MHC class I molecules produced by the TLR7 agonist alone and the checkpoint inhibitor alone in the mammal, and
wherein the human patient has a cancer and is refractory to the immune checkpoint inhibitor.

* * * * *